US011441125B2

(12) United States Patent
Endo et al.

(10) Patent No.: US 11,441,125 B2
(45) Date of Patent: Sep. 13, 2022

(54) METHOD FOR REESTABLISHMENT OF PLURIPOTENT STEM CELLS

(71) Applicant: JICHI MEDICAL UNIVERSITY, Tochigi (JP)

(72) Inventors: Hitoshi Endo, Tochigi (JP); Yasumitsu Nagao, Tochigi (JP); Yutaka Hanazono, Tochigi (JP); Kaoru Tominaga, Tochigi (JP); Tsukasa Ohmori, Tochigi (JP)

(73) Assignee: JICHI MEDICAL UNIVERSITY, Tochigi (JP)

( * ) Notice: Subject to any disclaimer, the term of this patent is extended or adjusted under 35 U.S.C. 154(b) by 548 days.

(21) Appl. No.: 15/516,107

(22) PCT Filed: Oct. 2, 2015

(86) PCT No.: PCT/JP2015/078699
§ 371 (c)(1),
(2) Date: Mar. 31, 2017

(87) PCT Pub. No.: WO2016/052759
PCT Pub. Date: Apr. 7, 2016

(65) Prior Publication Data
US 2017/0306296 A1    Oct. 26, 2017

(30) Foreign Application Priority Data

Oct. 2, 2014  (JP) .............................. JP2014-203679

(51) Int. Cl.
| C12N 5/073 | (2010.01) |
| C12N 5/0735 | (2010.01) |
| C12N 5/074 | (2010.01) |
| C12N 5/02 | (2006.01) |
| A01K 67/027 | (2006.01) |
| G01N 33/50 | (2006.01) |
| C12Q 1/02 | (2006.01) |
| C12N 15/09 | (2006.01) |
| C12Q 1/68 | (2018.01) |
| C12N 5/00 | (2006.01) |

(52) U.S. Cl.
CPC ........ *C12N 5/0696* (2013.01); *A01K 67/0271* (2013.01); *C12N 5/0604* (2013.01); *C12N 5/0606* (2013.01); *C12N 15/09* (2013.01); *C12Q 1/02* (2013.01); *G01N 33/5073* (2013.01); *A01K 67/027* (2013.01); *A01K 2207/12* (2013.01); *A01K 2267/02* (2013.01); *A01K 2267/03* (2013.01); *C12N 5/00* (2013.01); *C12N 2501/00* (2013.01); *C12Q 1/68* (2013.01)

(58) Field of Classification Search
None
See application file for complete search history.

(56) References Cited

U.S. PATENT DOCUMENTS

| 2007/0250943 A1 | 10/2007 | Nagao |
| 2013/0211187 A1 | 8/2013 | Araki |
| 2016/0073616 A1* | 3/2016 | Nakauchi ........... A01K 67/0271 800/3 |

FOREIGN PATENT DOCUMENTS

| WO | 2006/009297 A1 | 1/2006 |
| WO | 2012/029784 A1 | 3/2012 |
| WO | 2014/119627 A1 | 8/2014 |

OTHER PUBLICATIONS

Garry and Garry, Interspecies Chimeras and the Generation of Humanized Organs, Circulation Research Jan. 4, 2019, pp. 23-25.*
Suchy and Nakauchi, Lessons from Interspecies Mammalian Chimeras, Annu. Rev. Cell Dev. Biol. 2017. 33:203-17.*
De Los Angeles et al., Generating Human Organs via Interspecies Chimera Formation: Advances and Barriers , Yale Journal of Biology and Medicine 91 (2018), pp. 333-342.*
Levine adn Grabel, The contribution of human/non-human animal chimeras to stem cell research, Stem Cell Research, 2017, pp. 128-134.*
Bourretetal, Human-animal chimeras: ethical issues about farming chimeric animals bearing human organs , Cell Research & Therapy (2016) 7:87, pp. 1-7.*
Rashid et al, Revisiting the Flight of Icarus: Making Human Organs from PSCs with Large Animal Chimeras, Cell Stem Cell 15, Oct. 2, 2014, pp. 406-409.*
Yang et al., Derivation of Pluripotent Stem Cells with In Vivo Embryonic and Extraembryonic Potency, Cell 169, 243-257, Apr. 6, 2017.*
Tan et al, Chimeric contribution of human extended pluripotent stem cells to monkey embryos ex vivo, 2021, Cell 184, 2020-2032.*
Mascetti et al., Contributions of Mammalian Chimeras to Pluripotent Stem Cell Research, Cell Stem Cell 19, Aug. 4, 2016, pp. 163-175.*
Boroviak, T. et al., "The ability of inner-cell-mass cells to self-renew as embryonic stem cells is acquired following epiblast specification", Nature Cell Biology, May 25, 2014; 16(6): 513-525, including supplementary information, 23 pages.
Dan, J. et al., "Roles for Tbx3 in regulation of two-cell state and telomere elongation in mouse ES cells", Scientific Reports, Dec. 13, 2013; 3(3492): 1-9.
Fujishiro, S. et al., "Generation of Naive-Like Porcine-Induced Pluripotent Stem Cells Capable of Contributing to Embryonic and Fetal Development", Stem Cells and Development, Aug. 13, 2012; 22(3): 473-482.
Gafni, O. et al., "Derivation of novel human ground state naive pluripotent stem cells", Nature, Dec. 12, 2013; 504: 282-286, including supplementary information and corrigendum, 20 pages.

(Continued)

*Primary Examiner* — Maria Marvich
(74) *Attorney, Agent, or Firm* — Robin L. Teskin; Baker, Donelson, Bearman, Caldwell & Berkowitz PC

(57) ABSTRACT

The present application relates to a method for reestablishing stem cells capable of forming chimeras, and cells obtained by the method. The method of the present invention is a technique for monocloning stem cells, for example, capable of forming chimeras from a heterogeneous cell population to obtain high-quality stem cells.

20 Claims, 15 Drawing Sheets

Specification includes a Sequence Listing.

(56) References Cited

OTHER PUBLICATIONS

Hanna, J. et al., "Human embryonic stem cells with biological and epigenetic characteristics similar to those of mouse ESCs", PNAS, May 18, 2010, 107(20): 9222-9227.

* cited by examiner

Figure 2
(a) Pig iPS cells before selection
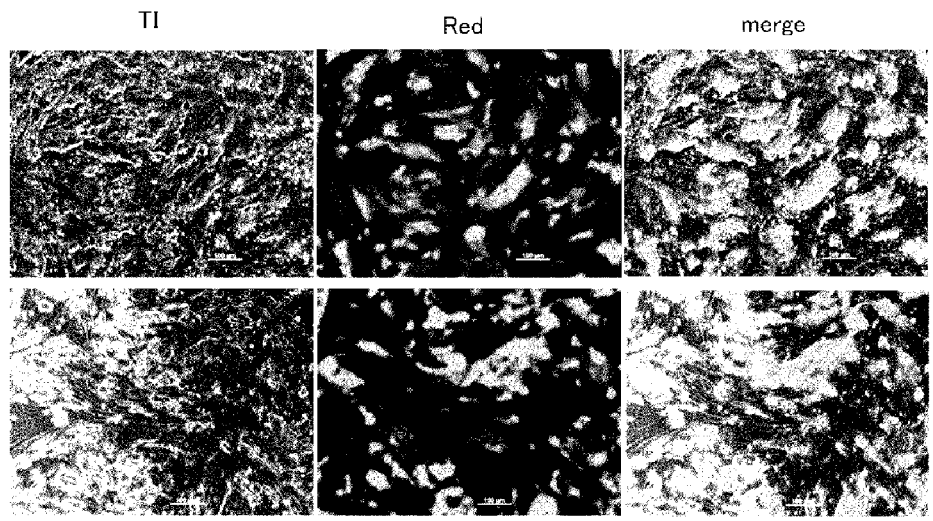
(b) Pig iPS cells after reestablishment
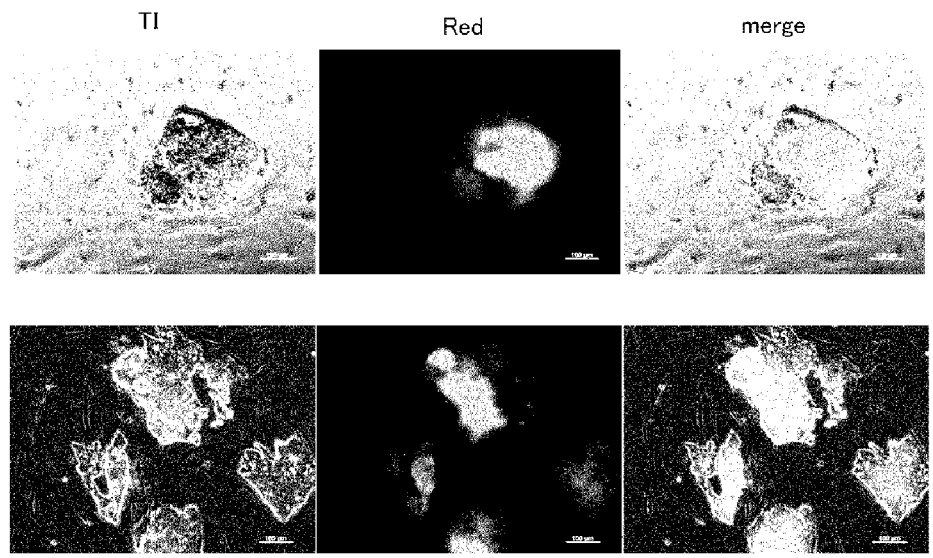

Figure 4
(a) E11.5 embryo
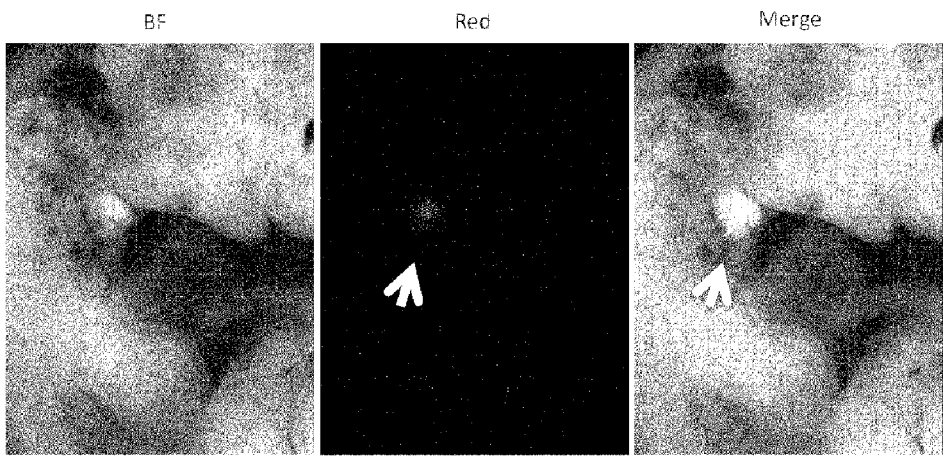
(b) E11.5 placenta
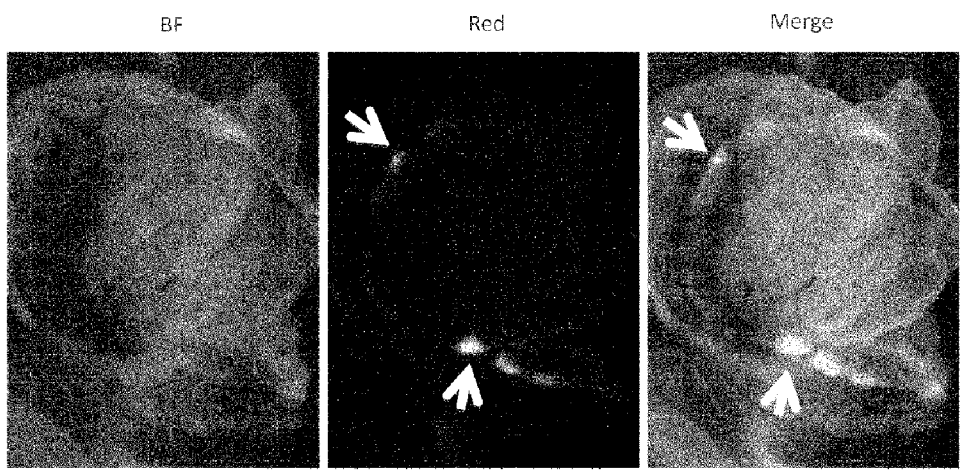

Figure 6
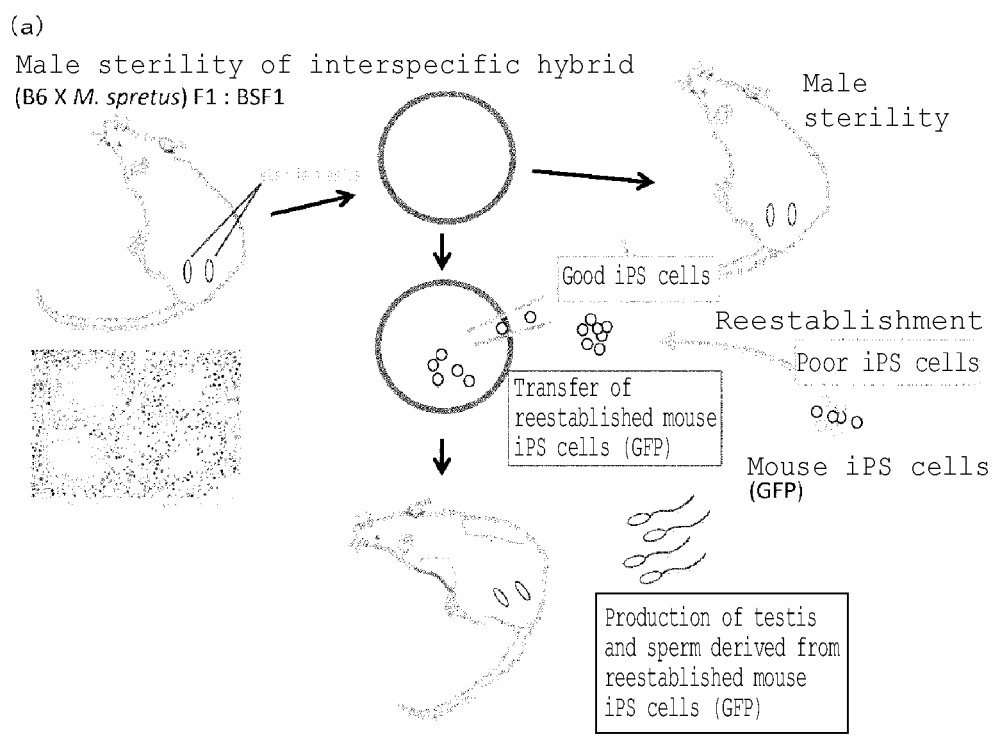
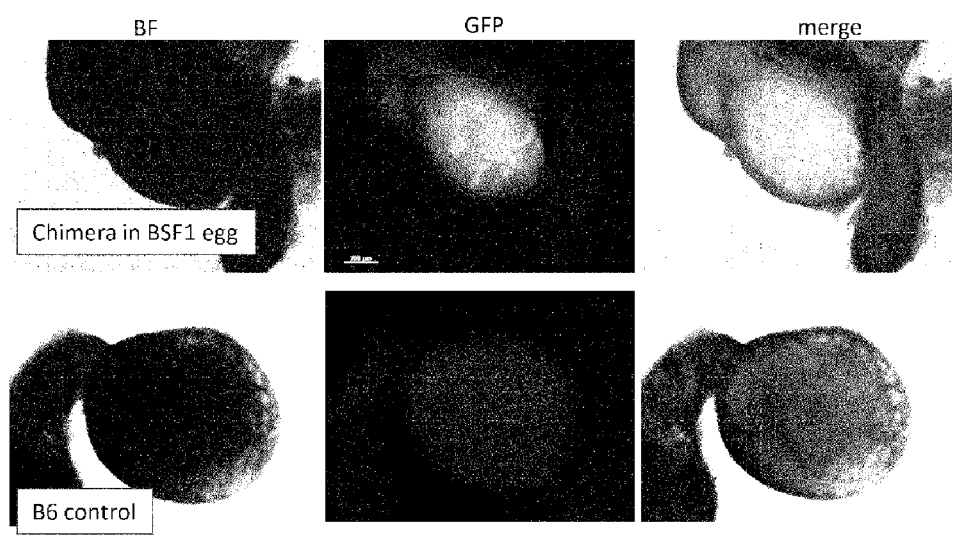

Figure 8

| gene_name | iPSC | | | Re-iPSC | | | iPSC_fpkm | Re-iPSC_fpkm | log2 (fold_change) iPSC vs Re-iPSC | significant ($q < 0.05$) |
|---|---|---|---|---|---|---|---|---|---|---|
| | TR_2160_021 (piPS3) | TR_2160_030 (piPS8) | TR_2160_031 (piPS9) | TR_2160_019 (piPS1) | TR_2160_023 (piPS5) | TR_2160_024 (piPS6) | | | | |
| NANOG | 6.64128 | 10.5605 | 4.77157 | 18.8449 | 18.7673 | 16.6241 | 7.32446 | 18.0788 | 1.3035 | yes |
| POU5F1 | 23.4072 | 25.014 | 0.94124 | 63.3492 | 66.101 | 62.5313 | 16.4541 | 63.9938 | 1.95948 | yes |
| KLF4 | 7.81948 | 7.80978 | 2.00803 | 27.6163 | 27.9558 | 26.4305 | 5.8791 | 27.3342 | 2.21704 | yes |
| SOX2 | 85.8584 | 98.2438 | 86.7792 | 101.25 | 99.6263 | 91.7042 | 90.2938 | 97.5269 | 0.111174 | no |
| MYC | 19.5931 | 23.5032 | 18.9592 | 18.2348 | 15.7873 | 16.0404 | 20.6851 | 16.6875 | -0.309827 | no |

Figure 9

| gene_name | iPSC | | | Re-iPSC | | | iPSC_fpkm | Re-iPSC_fpkm | log2 (fold change) iPSC vs Re-iPSC | significant ($q < 0.05$) |
|---|---|---|---|---|---|---|---|---|---|---|
| | TR 2160 021 (piPS3) | TR 2160 030 (piPS8) | TR 2160 031 (piPS9) | TR 2160 019 (piPS1) | TR 2160 023 (piPS5) | TR 2160 024 (piPS6) | | | | |
| hNANOG | 0.138944 | 0 | 0 | 0 | 0.246533 | 0.116265 | 0.0463145 | 0.120933 | 1.38467 | no |
| hPOU5F1 | 22393.5 | 24865.5 | 43663.9 | 9298.59 | 9927.86 | 10122.2 | 30307.7 | 9782.88 | -1.63135 | yes |
| hKLF4 | 1330.03 | 1849.32 | 1903.66 | 846.386 | 854.957 | 969.644 | 1694.34 | 890.329 | -0.92831 | yes |
| hSOX2 | 787.924 | 1071.53 | 1423.85 | 640.706 | 664.797 | 676.555 | 1094.43 | 660.686 | -0.728146 | yes |
| hMYC | 4768.11 | 6064.9 | 9973.61 | 2530.84 | 2601.57 | 2705.87 | 6935.54 | 2612.76 | -1.40843 | yes |

Figure 10

| Gene | gene expression ratio (Re-iPSC/iPSC) | |
| --- | --- | --- |
| | exo (human) | endo (pig) |
| NANOG | N.D. | Up |
| Oct4(Pou5f1) | Down | Up |
| KLF4 | Down | Up |
| Sox2 | Down | Not change |
| c-myc | Down | Down (no significance) |

Figure 12

Up-regulated genes in Re-iPSCs

| Category | Term | Count | % | P Value |
|---|---|---|---|---|
| SP_PIR_KEYWORDS | glycoprotein | 61 | 38.85350318 | 3.47E-06 |
| SP_PIR_KEYWORDS | Tight junction | 6 | 3.821656051 | 1.32E-04 |
| GOTERM_BP_FAT | GO:0007155~cell adhesion | 17 | 10.82802548 | 0.001288226 |
| GOTERM_BP_FAT | GO:0048598~embryonic morphogenesis | 9 | 5.732484076 | 0.010449095 |
| SP_PIR_KEYWORDS | extracellular matrix | 10 | 6.369426752 | 1.51E-04 |
| SP_PIR_KEYWORDS | protease inhibitor | 5 | 3.184713376 | 0.011024541 |

Down-regulated genes in Re-iPSCs

| Category | Term | Count | % | P Value |
|---|---|---|---|---|
| GOTERM_BP_FAT | GO:0060429~epithelium development | 7 | 10 | 1.79E-04 |
| GOTERM_BP_FAT | GO:0010035~response to inorganic substance | 5 | 7.142857143 | 0.006844212 |
| UP_SEQ_FEATURE | calcium-binding region:1 | 4 | 5.714285714 | 0.010682556 |

METHOD FOR REESTABLISHMENT OF PLURIPOTENT STEM CELLS

RELATED APPLICATIONS

This application is a 371 National Stage filing of International Application No. PCT/JP2015/078699, filed Oct. 2, 2015, which claims the benefit of Japanese Application No. 2014-203679, filed Oct. 2, 2014, each of which is hereby incorporated by reference in its entirety.

SEQUENCE LISTING

This application includes as part of its disclosure a biological sequence listing text file named "49416o1201.txt" having a size of 1,044 bytes that was created Mar. 30, 2017, which is hereby incorporated by reference in its entirety.

TECHNICAL FIELD

The present application relates to a method for reestablishing stem cells capable of forming chimeras from pluripotent stem cells or multipotent stem cells. The method is a technique for selecting and reestablishing cells having, for example, the property of maintaining the capability of forming chimeras from pluripotent stem cells or multipotent stem cells to obtain high-quality stem cells. The present application also relates to stem cells capable of forming chimeras, reestablished by the method. The present application further relates to a method for conducting drug efficacy evaluation or pathological analysis using stem cells capable of forming chimeras, reestablished by the method of the present invention, or somatic stem cells, organ progenitor cells, or somatic cells obtained by the differentiation of the stem cells.

BACKGROUND ART

The preparation or supply of organ anlagen or organ stem cells from iPS cells (induced pluripotent stem cells) or ES cells (embryonic stem cells) is necessary for the development of regenerative medicine using iPS cells or the like. For example, for the transplantation of human organs or organ anlagen regenerated from iPS cells or ES cells to humans, the step of inducing the cells to the formation of the organs of interest in a heterospecific environment such as pigs or sheep is considered to be effective. However, since organ anlagen or organ stem cells are difficult to prepare in vitro, it is necessary to prepare chimeric embryos between different species and collect organ anlagen or organ stem cells from the chimeric embryos. For this purpose, high-quality stem cells that are engraftable between different species and maintain the capability of forming chimeras need to be used as starting cells for organ formation.

The preparation of clone animals or chimeric animals from iPS cells or ES cells is considered to be useful from the viewpoint of the preservation, regeneration, or maintenance of rare species of animals such as endangered species, companion mammals such as pet animals, or useful commercial animals. In this case, high-quality stem cells that are engraftable between the same species or between different species and maintain the capability of forming chimeras need to be used as starting cells.

Mouse or rat ES cells have generally been established as naive pluripotent stem cells, and there are a plurality of reports on the preparation of chimeric animals by a blastocyst complementation method. Meanwhile, the colonies of iPS or ES cells of middle animals such as rabbits, pigs, monkeys, or humans are characteristically flat in a primed form, and these cells cannot form chimeras even if transplanted to heterospecific or conspecific blastocysts, or contribute to chimeras, if any, at a very small rate.

Thus, importance of the method for reestablishing stem cells capable of forming chimeras has been increasing from the viewpoint of enhancing the success rate of preparation of chimeric embryos or chimeric animals.

According to most of previous reports with the aim of obtaining iPS cells or ES cells capable of forming chimeras, the iPS cells or the ES cells have been established by an approach such as gene transfection (Non Patent Literature 1). According to another report, iPS cells or ES cells having high quality have been established by the modification of a medium by, for example, the addition of an environmental factor (Non Patent Literature 2). Although the techniques of these reports are to prepare iPS cells or ES cells capable of forming chimeras, the prepared iPS cells or ES cells are heterogeneous cell populations and have not been sufficiently evaluated for denying the possibility that cells incapable of forming chimeras coexist therewith. These techniques are techniques of increasing the ratio of cells "capable of forming chimeras" to iPS cells or ES cells.

At present, cells that maintain the property of being "capable of forming chimeras" account for only a portion of all cells obtained in the establishment of iPS cells or ES cells. For obtaining starting cells for organ formation, etc., it is necessary to further screen the established iPS cells or ES cells and reestablish the selected cells to obtain high-quality stem cells, from the viewpoint of the maintenance of the acquired capability of forming chimeras.

Nagao et al. (Patent Literature 1) disclose pluripotent cells lacking a function involving a particular gene by the mutation or deletion of the gene, and a method for preparing a chimeric animal, comprising injecting two or more types of cells including additional pluripotent cells other than the pluripotent cells to an animal host embryo. Patent Literature 1 states that it was found that ES cells are efficiently established from reproductive organ-derived cells by establishing ES cells from a mouse embryo incapable of forming germ cells, and coculturing the ES cells with animal reproductive organ-derived cells. This literature also states that it was found that the proliferative capacity of additional mouse ES cells, for example, genetically modified ES cells, can be improved by coculturing the ES cells established from a mouse embryo incapable of forming germ cells with the additional mouse ES cells.

However, at present, there is no report on a method that permits reestablishment of iPS or ES cells capable of forming chimeras, regardless of being conspecific or heterospecific.

CITATION LIST

Patent Literature

Patent Literature 1: International Publication No. WO2006/009297

Non Patent Literature

Non Patent Literature 1: Hanna, J., et al., Proc. Natl. Acad. Sci. USA, 107: 9222-9227 (2010)
Non Patent Literature 2: Gafni, O., et al., Nature, 504 (7479): 282-286 (2013)
Non Patent Literature 3: Nature Cell Biology, 16: 513 (2014)
Non Patent Literature 4: Scientific Rep. 3: 3492 (2013)

SUMMARY OF INVENTION

Technical Problem

As mentioned above, for obtaining starting cells for organ formation, etc., there is still a demand for a method which involves further screening established iPS cells or ES cells and reestablishing the selected cells to obtain high-quality stem cells, from the viewpoint of the maintenance of the acquired capability of forming chimeras. An object of the present invention is to provide a method for reestablishing stem cells capable of forming chimeras. Another object of the present invention is to provide reestablished stem cells capable of forming chimeras.

Solution to Problem

The present inventors have conducted diligent studies to attain the objects. For preparing organ anlagen or organ stem cells from iPS cells or ES cells, high-quality stem cells that are engraftable between different species and maintain the capability of forming chimeras need to be supplied as starting cells for organ formation. For solving this challenge, it is necessary to develop a system that can prepare "good iPS or ES cells" capable of forming chimeras between different species. As one of the methods therefor, the present inventors have developed a "system for coculture and reestablishment between different species". Specifically, as the "system for coculture and reestablishment between different species", the present inventors have found a method for reestablishing an iPS cell or ES cell line as stem cells that maintain the capability of forming chimeras, comprising (1) coculturing iPS cells or ES cells with high-quality pluripotent stem cells (e.g., iPS cells, ES cells, or an inner cell mass containing these cells) of a different species from the iPS cells or the ES cells, followed by selection under conditions based on whether to be a cell group that contributes to the formation of a naive colony formed by ES cells; and/or (2) transplanting iPS cells or ES cells to a host embryo (e.g., a mouse early embryo such as a morula, a blastocyst, or a tetraploid embryo) of a different species from the iPS cells or the ES cells by microinjection or the like and coculturing the cells with the host embryo, followed by selection under conditions based on whether to be capable of contributing to the formation of an inner cell mass (ICM); and, if necessary, repeating the steps (1) and/or (2) described above. The present inventors have transplanted pig iPS cells reestablished by the method described above to a mouse embryo and consequently successfully established a plurality of lines of iPS cells that contribute to chimeras of E11.5 embryos. In addition, this method has been positioned as a method which involves placing a heterogeneous cell group of pluripotent stem cells prepared by an existing method in an environment or a host embryo where high-quality pluripotent stem cells coexist therewith so that the heterogeneous cell group is adapted and acclimatized as a cell group capable of forming chimeras, and then selecting the cell group capable of forming chimeras. On the basis of these study results, the present invention has been completed.

Furthermore, the present inventors have gained the technical thought that such a system for coculture and reestablishment between different species can also be used as a system that can prepare iPS cells or ES cells capable of forming chimeras between the same species.

Specifically, in one aspect, the present invention may provide the following:

(1) A method for reestablishing stem cells capable of forming chimeras between different species, comprising the following steps:

(i) coculturing first mammalian species-derived pluripotent stem cells or multipotent stem cells with second mammalian species-derived high-quality pluripotent stem cells;

(ii) selecting a cell group comprising stem cells that form a cell assembly in the cocultures of the step (i) and are derived from the first mammalian species-derived pluripotent stem cells or multipotent stem cells;

(iii) coculturing the cell group of the step (ii) with a second mammalian species-derived host embryo;

(iv) separating an inner cell mass from the host embryo cocultured in the step (iii); and (v) cloning, from the inner cell mass, the stem cells derived from the first mammalian species-derived pluripotent stem cells or multipotent stem cells to reestablish stem cells capable of forming chimeras between different species, wherein the first mammalian species and the second mammalian species are different species, and the first mammalian species-derived pluripotent stem cells or multipotent stem cells are non-rodent mammalian species-derived pluripotent stem cells or multipotent stem cells or are rodent-derived induced pluripotent stem cells (iPS cells) or multipotent stem cells.

(2) The method according to (1), further comprising combining the stem cells reestablished in the step (v) with the second mammalian species-derived high-quality pluripotent stem cells to obtain a cell group, and repeating the steps (iii) to (v).

(3) The method according to (1) or (2), wherein the pluripotent stem cells are selected from the group consisting of the following: ES cells and induced pluripotent stem cells (iPS cells), and the multipotent stem cells are selected from the group consisting of the following: trophoblast stem cells (TS cells), epiblast stem cells (EpiS cells), embryonic genu cells (EG cells), multipotent germline stem cells (mGS cells), nuclear transfer ES cells (ntES cells), hematopoietic stem cells, neural stem cells, and mesenchymal stem cells.

(4) The method according to any one of (1) to (3), wherein the first mammalian species-derived pluripotent stem cells or multipotent stem cells are ES cells or iPS cells.

(5) The method according to any one of (1) to (4), wherein the high-quality pluripotent stem cells are naive pluripotent stem cells.

(6) The method according to any one of (1) to (5), wherein the host embryo is selected from the group consisting of an early embryo, a tetraploid embryo, a male embryo, a parthenogenetic embryo, and ES cells contributing to a placenta.

(7) The method according to any one of (1) to (6), wherein the step (iii) is performed by microinjecting or aggregating the cell group of the step (ii) to the second mammalian species-derived early embryo or tetraploid embryo, followed by coculture.

(8) The method according to any one of (1) to (7), wherein the first mammalian species and the second mammalian species are each selected from the group consisting of a mouse, a rat, a rabbit, a dog, a cat, a horse, cattle, a goat, sheep, a pig, a monkey, and a human.

(9) A method for reestablishing stem cells capable of forming chimeras between different species, comprising the following steps:

(i) combining first mammalian species-derived pluripotent stem cells or multipotent stem cells with second mammalian species-derived high-quality pluripotent stem cells to obtain a cell group;

(ii) coculturing the cell group of the step (i) with a second mammalian species-derived host embryo;

(iii) separating an inner cell mass from the host embryo cocultured in the step (ii); and (iv) cloning, from the inner cell mass, stem cells derived from the first mammalian species-derived pluripotent stem cells or multipotent stem cells to reestablish stem cells capable of forming chimeras between different species, wherein the first mammalian species and the second mammalian species are different species, and the first mammalian species-derived pluripotent stem cells or multipotent stem cells are non-rodent mammalian species-derived pluripotent stem cells or multipotent stem cells or are rodent-derived induced pluripotent stem cells (iPS cells) or multipotent stem cells.

(10) The method according to (9), further comprising repeating the steps (i) to (iv), wherein the step (i) of the 2nd cycle or later is performed by combining the stem cells reestablished in the step (iv) of the preceding cycle with the second mammalian species-derived high-quality pluripotent stem cells to obtain a cell group.

(11) The method according to any one of (1) to (10), wherein the first mammalian species-derived pluripotent stem cells are not human ES cells, and the second mammalian species is not a human.

(12) A method for reestablishing stem cells capable of forming chimeras between the same species, comprising the following steps:

(i) coculturing mammalian species-derived pluripotent stem cells or multipotent stem cells with conspecific mammal-derived high-quality pluripotent stem cells;

(ii) selecting a cell group comprising stem cells that form a cell assembly in the cocultures of the step (i) and are derived from the pluripotent stem cells or the multipotent stem cells;

(iii) coculturing the cell group of the step (ii) with a conspecific mammal-derived host embryo;

(iv) separating an inner cell mass from the host embryo cocultured in the step (iii); and (v) cloning, from the inner cell mass, the stem cells derived from the pluripotent stem cells or the multipotent stem cells to reestablish stem cells capable of forming chimeras between the same species, wherein the mammalian species-derived pluripotent stem cells or multipotent stem cells are non-rodent mammalian species-derived pluripotent stem cells or multipotent stem cells or are rodent-derived induced pluripotent stem cells (iPS cells) or multipotent stem cells.

(13) The method according to (12), further comprising combining the stem cells reestablished in the step (v) with the conspecific mammal-derived high-quality pluripotent stem cells to obtain a cell group, and repeating the steps (iii) to (v).

(14) A method for reestablishing stem cells capable of forming chimeras between the same species, comprising the following steps:

(i) combining mammalian species-derived pluripotent stem cells or multipotent stem cells with conspecific mammal-derived high-quality pluripotent stem cells to obtain a cell group;

(ii) coculturing the cell group of the step (i) with a conspecific mammal-derived host embryo;

(iii) separating an inner cell mass from the host embryo cocultured in the step (ii); and (iv) cloning, from the inner cell mass, stem cells derived from the pluripotent stem cells or the multipotent stem cells to reestablish stem cells capable of forming chimeras between the same species, wherein the mammalian species-derived pluripotent stem cells or multipotent stem cells are non-rodent mammalian species-derived pluripotent stem cells or multipotent stem cells or are rodent-derived induced pluripotent stem cells (iPS cells) or multipotent stem cells.

(15) The method according to (14), further comprising repeating the steps (i) to (v), wherein the step (i) of the 2nd cycle or later is performed by combining the stem cells reestablished in the step (iv) of the preceding cycle with the conspecific mammal-derived high-quality pluripotent stem cells to obtain a cell group.

(16) The method according to any one of (12) to (15), wherein the mammalian species is not a human.

(17) Stem cells reestablished from non-rodent mammalian species-derived pluripotent stem cells or multipotent stem cells or from rodent-derived iPS cells or multipotent stem cells, wherein the stem cells have one or more features selected from the group consisting of the following:

being capable of forming chimeras;

being capable of forming a cell assembly; and having high affinity for the niche environment of an inner cell mass.

(18) The cells according to (17), wherein the cells are cells reestablished by a method according to any one of (1) to (16).

(19) A method for conducting drug efficacy evaluation or pathological analysis using cells, comprising the following steps:

(i) obtaining cells, wherein the cells are (A) stem cells capable of forming chimeras, reestablished by a method according to any one of (1) to (16) or (B) somatic stem cells, organ progenitor cells, or somatic cells obtained by the differentiation of stem cells capable of forming chimeras, reestablished by a method according to any one of (1) to (16), wherein the somatic stem cells, the organ progenitor cells, or the somatic cells are obtained by any of the following methods (a) to (c):

(a) preparing a chimeric embryo or a chimeric fetus from the stem cells capable of forming chimeras, reestablished by a method according to any one of (1) to (16), and obtaining somatic stem cells, organ progenitor cells, or somatic cells derived from the chimeric embryo or the chimeric fetus;

(b) differentiating in vitro the somatic stem cells derived from the chimeric embryo or the chimeric fetus obtained in method (a) to obtain organ progenitor cells or somatic cells; and (c) differentiating in vitro the stem cells capable of forming chimeras, reestablished by a method according to any one of (1) to (16) to obtain somatic stem cells, organ progenitor cells, or somatic cells; and (ii) conducting drug efficacy evaluation or pathological analysis using the cells obtained in the step (i).

Advantageous Effects of Invention

According to the method of the present invention, a heterogeneous cell group of pluripotent stem cells, etc. prepared by an existing method can be placed in an environment or a host embryo environment where high-quality pluripotent stem cells coexist therewith so that the heterogeneous cell group is adapted and acclimatized as a cell group capable of forming chimeras, and then, the cell group capable of forming chimeras can be selected. The existing method for establishing pluripotent stem cells or the like is a technique for increasing the ratio of cells "capable of forming chimeras between different species", whereas the method of the present invention is a technique for removing, for refinement, cells "incapable of forming chimeras between different species", which may coexist with the cells of interest, to complete a transplantable line. The method of the present invention is useful for providing high-quality cells necessary as starting cells for organ transplantation, etc., using iPS cells or ES cells in regenerative medicine.

Chimeric embryo- or fetus-derived somatic cells, organ progenitor cells, or somatic stem cells can be obtained by a method which involves, for example, preparing a chimeric embryo or fetus from stem cells capable of forming chimeras, selected by the method of the present invention, and separating or establishing somatic cells or organ progenitor cells from the chimeric embryo or fetus, separating or establishing somatic stem cells from the chimeric embryo or fetus, or preparing somatic cells including organ progenitor cells differentiated from the somatic stem cells. Alternatively, the stem cell-derived somatic stem cells, organ progenitor cells, or somatic cells can also be obtained by the in vitro differentiation of stem cells capable of forming chimeras, selected by the method of the present invention. These chimeric embryo- or fetus-derived cells or cells obtained by the in vitro differentiation of the stem cells capable of forming chimeras are useful for use in drug efficacy evaluation, regenerative medicine, etc.

BRIEF DESCRIPTION OF THE SEVERAL VIEWS OF THE DRAWINGS

FIG. 2 is a photograph showing the morphology of (a) pig iPS cells before selection and (b) pig iPS cells after reestablishment. The scale represents 100 μm.

FIG. 4 is a photograph showing that chimeric animals were prepared using reestablished iPS cells. Panel (a) is a photograph showing an embryo. From the presence of red fluorescent protein, it was confirmed that cells derived from the pig iPS cells were present in the embryo. Panel (b) is a photograph showing a placenta. It was confirmed that cells derived from the pig iPS cells were present in the amnion.

FIG. 6 is a diagram showing that chimeric mice were prepared by a blastocyst complementation method based on a chimera method using iPS cells capable of forming chimeras between the same species, reestablished by the method of the present application. Panel (a) is a schematic diagram showing procedures of preparing a chimeric mouse. Panel (b) is a photograph showing that cells derived from the iPS cells were present in the testis of a chimeric mouse embryo (embryonic age: 18.5) (iPS cells were labeled with the green fluorescent protein).

FIG. 8 is a diagram showing the gene expression levels of endogenous genes of four Yamanaka factors and NANOG.

FIG. 9 is a diagram showing the gene expression levels of human genes (exogenous genes) of four Yamanaka factors and NANOG in pigs transfected therewith.

FIG. 10 is a diagram summarizing the results about change in the gene expression of foreign and endogenous four Yamanaka factors and NANOG between before and after reestablishment (FIGS. 8 and 9).

FIG. 12 is a diagram summarizing the types of genes whose expression in reestablished cells was increased by 2 or more in terms of a $\log_2$ value as compared with cells before reestablishment, and the types of genes whose expression in reestablished cells was decreased as compared with cells before reestablishment.

DESCRIPTION OF EMBODIMENTS

Figure 1:
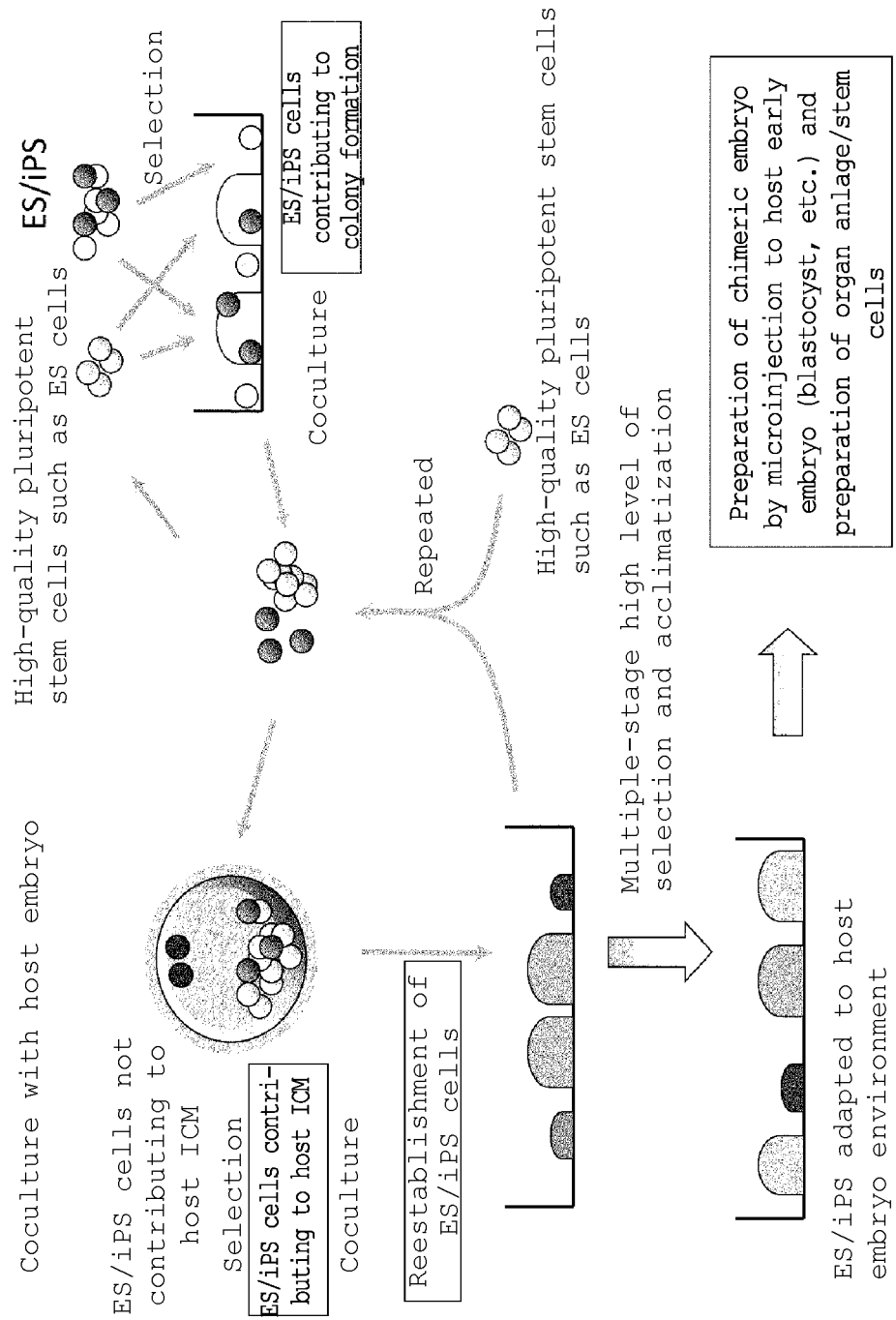
FIG. 1 is a schematic diagram showing one aspect of the method for reestablishing stem cells capable of forming chimeras according to the present application.

Hereinafter, the present invention will be specifically described. However, the present invention is not intended to be limited to these embodiments.

The present invention relates to a method for reestablishing stem cells capable of forming chimeras between different species or between the same species, stem cells capable of forming chimeras between different species or between the same species, and a method for conducting drug efficacy evaluation or pathological analysis using the stem cells or cells obtained by the differentiation of the stem cells.

Definition

In the present specification, scientific terms and technical terms used in relation to the present invention have meanings generally understood by those skilled in the art, unless otherwise specified.

In the present specification, the "stem cells" are cells having the ability to self-renew and differentiation capacity. In this context, the ability to self-renew refers to the ability to replicate a cell having the same ability as in oneself. The differentiation capacity refers to the ability to differentiate into a plurality of cells having different functions.

In the present specification, the "pluripotent stem cells" are stem cells and are cells having the ability to differentiate into every type of cell constituting an individual. The pluripotent stem cells include embryonic stem cells (ES cells) and induced pluripotent stem cells (iPS cells).

In the present specification, the "multipotent stem cells" are stem cells and are cells having the ability to differentiate into plural types of cells. The multipotent stem cells include, for example, trophoblast stem cells (TS cells), epiblast stem cells (EpiS cells), embryonic germ cells (EG cells), multipotent germline stem cells (mGS cells), nuclear transfer ES cells (ntES cells), hematopoietic stem cells, neural stem cells, and mesenchymal stem cells.

In the present specification, the phrase "pluripotent stem cells, etc." is understood to include pluripotent stem cells and multipotent stem cells.

The preparation of a chimeric embryo or a chimeric animal is performed by transplanting the pluripotent stem cells, etc. to a fertilized egg, an early embryo, or the like of a host (another individual), followed by development. The chimeric embryo is prepared from the transplanted pluripotent stem cells, etc. that have become the whole or a portion of the resulting host embryonic body. The chimeric animal is prepared from the transplanted pluripotent stem cells, etc. that have become a portion of the resulting individual.

In the present specification, the phrase "capable of forming chimeras" regarding stem cells means that, when the stem cells are transplanted to a fertilized egg, an early embryo, or the like of a host, the stem cells have the ability to become the whole or a portion of the resulting host embryonic body or a portion of various organs in the resulting individual. Alternatively, in the present specification, the phrase "capable of forming chimeras" regarding stem cells is also used as a phrase meaning that, when the stem cells are transplanted to a fertilized egg, an early embryo, or the like of a host, the stem cells have the ability to constitute a portion of an inner cell mass (ICM) by the transplanted pluripotent stem cells, etc., i.e., the ability to contribute to ICM. In this context, in the case where the species from which the stem cells to be transplanted are derived and the species of the host are different species, the phrase "capable of forming chimeras between different species" is particularly used. In the case where the species from which the stem cells to be transplanted are derived and the species of the host are the same species, the phrase "capable of forming chimeras between the same species" is particularly used.

In the present specification, the term "heterospecific" or "different species" means that animal species are different from each other. The term "heterospecific" or "different species" means that animal species are different from each other at a genus or higher level, unless otherwise specified.

In the present specification, the term "conspecific" or "same species" means belonging to the same animal species. The range of the term "conspecific" or "same species" includes not only belonging to the same animal species at a species level but belonging to the same animal species at a genus level, i.e., "congeneric", unless otherwise specified.

In the present specification, the "high quality" regarding pluripotent stem cells, etc. means that the pluripotent stem cells, etc. are "naive". The "naive" pluripotent stem cells, etc. mean that the pluripotent stem cells, etc. have one or more, preferably two or more, more preferably all three properties selected from the group consisting of forming a dome-shaped colony, being capable of forming chimeras, and being capable of differentiating into a germline such as sperms or ova.

In the present specification, the "host embryo" means an embryo of a host animal to which pluripotent stem cells are transplanted in the preparation of a chimeric embryo or a chimeric animal.

<Method for Reestablishing Stem Cells Capable of Forming Chimeras Between Different Species>

The present application provides a method for reestablishing stem cells capable of forming chimeras between different species.

In the first embodiment, the present application provides a method for reestablishing stem cells capable of forming chimeras between different species, comprising the following steps:

(i) coculturing first mammalian species-derived pluripotent stem cells or multipotent stem cells with second mammalian species-derived high-quality pluripotent stem cells;

(ii) selecting a cell group comprising stem cells that form a cell assembly in the cocultures of the step (i) and are derived from the first mammalian species-derived pluripotent stem cells or multipotent stem cells;

(iii) coculturing the cell group of the step (ii) with a second mammalian species-derived host embryo;

(iv) separating an inner cell mass from the host embryo cocultured in the step (iii); and (v) cloning, from the inner cell mass, the stem cells derived from the first mammalian species-derived pluripotent stem cells or multipotent stem cells to reestablish pluripotent stem cells or multipotent stem cells capable of forming chimeras, wherein the first mammalian species and the second mammalian species are different species, and the first mammalian species-derived pluripotent stem cells or multipotent stem cells are non-rodent mammalian species-derived pluripotent stem cells or multipotent stem cells or are rodent-derived induced pluripotent stem cells (iPS cells) or multipotent stem cells.

The method may further comprise combining the stem cells reestablished in the step (v) with the second mammalian species-derived high-quality pluripotent stem cells to obtain a cell group, and repeating the steps (iii) to (v). The cell group can be obtained by every method that can allow the stem cells reestablished in the step (v) to coexist with the second mammalian species-derived high-quality pluripotent stem cells, or mix therewith the stem cells reestablished in the step (v).

In the method, the "pluripotent stem cells" are selected from the group consisting of ES cells and induced pluripotent stem cells (iPS cells). The "multipotent stem cells" are selected from the group consisting of trophoblast stem cells (TS cells), epiblast stem cells (EpiS cells), embryonic germ cells (EG cells), multipotent germline stem cells (mGS cells), nuclear transfer ES cells (ntES cells), hematopoietic stem cells, neural stem cells, and mesenchymal stem cells. In a preferred embodiment, the "pluripotent stem cells or multipotent stem cells" are ES cells or iPS cells. The "high-quality pluripotent stem cells" include ES cells, iPS cells, or an inner cell mass of these cells. The "high-quality pluripotent stem cells" are preferably ES cells.

In the method, the mammalian species are not particularly limited as long as the mammalian species are mammals. The first mammalian species and the second mammalian species are different species and may be each independently selected from the group described below. In a preferred embodiment, the first or second mammalian species is selected from the group consisting of a mouse, a rat, a rabbit, a dog, a cat, a horse, cattle, a goat, sheep, a pig, a monkey, and a human and more preferably selected from the group consisting of a mouse, a rat, a pig, a monkey, and a human. Particularly preferably, the first mammalian species is selected from the group consisting of a pig, a monkey, and a human.

In the step (i) of the method, first mammalian species-derived pluripotent stem cells or multipotent stem cells are cocultured with second mammalian species-derived high-quality pluripotent stem cells. In the step, the coculture is performed in vitro under conditions suitable for the culture of first mammalian species-derived naive pluripotent stem cells or multipotent stem cells or conditions suitable for the culture of the second mammalian species-derived high-quality pluripotent stem cells, or mixed conditions thereof. Those skilled in the art can appropriately set the type of a medium and culture conditions such as culture temperature and culture time, suitable for the culture of these cells.

In the case of coculturing, for example, pig iPS cells with mouse ES cells, the coculture is carried out under such optimum conditions that the culture is first performed under mouse ES cell culture conditions, which are gradually changed to naive pig iPS cell culture conditions. In this respect, examples of the culture conditions include conditions involving gas concentrations of 5% $CO_2$ and 95% air and a culture temperature of 37° C. to 39° C. For example, pig iPS cells fluorescently labeled with Kusabira Orange are mixed with mouse ES cells to prepare cell masses. The cell masses are inoculated to dishes coated with feeder cells. MEF (mouse embryonic fibroblast) is used as the feeder cells. Colonies in a favorable mosaic state are collected by selection using various selective markers such as fluorescent proteins and visual selection of morphology favorable for cloning. After further inoculation of the colonies, a colony in a good state having the selective marker such as fluorescence is selected from newly formed colonies. In this respect, the medium conditions are, for example, such optimum conditions that the culture is first performed under mouse ES cell medium conditions, which are gradually changed to naive pig iPS cell culture conditions. For example, the following medium composition can be used.

Medium composition for naive pig iPS cells: a culture solution containing 82% (v/v) D-MEM, 15% (v/v) FCS, 0.1 mM 2-mercaptoethanol, 1×MEM nonessential amino acid solution, 1× GlutaMAX™-I (GIBCO), 1× rhLIF (Wako Pure Chemical Industries, Ltd.), and 10 µM forskolin.

Culture composition for mouse ES cells: a culture solution containing 80% (v/v) D-MEM, 20% (v/v) FCS, 1 mM pyruvic acid solution, 0.1 mM 2-mercaptoethanol, 1×MEM nonessential amino acid solution, and $10^3$ U/mL mLIF.

In the step (ii) of the method, a cell group comprising stem cells that form a cell assembly in the cocultures of the step (i) and are derived from the first mammalian species-derived pluripotent stem cells or multipotent stem cells is selected. Specifically, this step is the step of selecting a cell group comprising stem cells derived from the first mammalian species-derived pluripotent stem cells or multipotent stem cells that form a colony (particularly, a naive colony) together with the second mammalian species-derived high-quality pluripotent stem cells. In such a case where stem cells form a colony together with ES cells, the stem cells are also expressed as "stem cells that contribute to colony formation". The selection of the cell group comprising stem cells derived from the first mammalian species-derived pluripotent stem cells, etc. that form a colony (particularly, a naive colony) together with the second mammalian species-derived high-quality pluripotent stem cells can be performed by labeling the first mammalian species-derived pluripotent stem cells, etc. with an appropriate selective marker before the selection, and selecting a colony containing the selective marker. Alternatively, the second mammalian species-derived high-quality pluripotent stem cells may be labeled with an appropriate selective marker, and a colony free from the selective marker can be identified as a cell group comprising the first mammalian species-derived pluripotent stem cells, etc. Examples of the appropriate selective marker include Kusabira Orange (huKO), green fluorescent protein (GFP), Clover, DsRed, mCherry, luciferase, LacZ, neomycin resistance gene, puromycin resistance gene, hygromycin B resistance gene, blasticidin resistance gene, zeocin resistance gene, DT-A gene, and HSV-TK gene. The identification can be performed by identification based on fluorescence, luminescence, staining, etc., or drug selection using a drug resistance gene or the like.

In the step (iii) of the method, the cell group of the step (ii) is cocultured with a second mammalian species-derived host embryo. A chimeric embryo is prepared by the coculture of the cell group of the step (ii) with the second mammalian species-derived host embryo. In the coculture of the step (iii), the chimeric embryo is then cultured until an early blastocyst stage where an inner cell mass (ICM) is obtained. In a preferred embodiment, the coculture of this step is performed by microinjecting or aggregating the cell group of the step (ii) to the second mammalian species-derived host embryo, followed by coculture. The microinjection is a method which involves transplanting cells (stem cells, etc.) to a host embryo to prepare a chimeric embryo. The aggregation is a method which involves using an early embryo up to a morula stage as a host embryo and contacting or assembling stem cells, etc. with this early embryo to prepare a chimeric embryo. More preferably, the coculture of the step (iii) is performed by microinjecting the cell group of the step (ii) to the second mammalian species-derived host embryo, followed by coculture.

The host embryo is not particularly limited and may be selected from an early embryo, a tetraploid embryo, a male embryo, a parthenogenetic embryo, and ES cells contributing to a placenta. In a preferred embodiment, the host embryo is an early embryo or a tetraploid embryo.

The early embryo means an embryo from a two-cell embryo to a blastocyst-stage embryo.

The tetraploid embryo is an embryo prepared by the electrical fusion of wild-type two-cell blastomeres. If the chimeric embryo is prepared by the coculture of pluripotent stem cells using the tetraploid embryo, the resulting embryonic body or individual is derived 100% from the pluripotent stem cells because tetraploid cells cannot contribute to an embryonic body itself, but has the property of being capable of contributing to extraembryonic tissues such as placentae.

The male embryo is an embryo that is unlikely to become a fetus in itself. However, a fetus can be obtained by preparing a chimeric embryo by the coculture of pluripotent cells with the male embryo.

The parthenogenetic embryo is an embryonic lethal embryo in itself. However, an individual may be obtained by preparing a chimeric embryo by the coculture of pluripotent cells with the parthenogenetic embryo.

The ES cells contributing to a placenta are totipotent cells present as a very minor subpopulation contained in a cell population of ES cells. It was generally considered that ES cells are derived from a blastocyst-stage embryo, functionally correspond to an inner cell mass, and do not form extraembryonic tissues such as placentae. However, it has been reported that very few fractions of ES cells contain a cell group corresponding to two-cell embryos having totipotency (Macfarlan, T. S., et al., Nature, 487 (7405): 57-63 (2012)). This cell group having totipotency is particularly referred to as ES cells contributing to a placenta.

Preferably, the step (iii) of the method is performed by microinjecting or aggregating the cell group of the step (ii) to the second mammalian species-derived early embryo or tetraploid embryo, followed by coculture. More preferably, the step (iii) of the method is performed by microinjecting the cell group of the step (ii) to the second mammalian species-derived early embryo or tetraploid embryo, followed by coculture.

In the step (iv) of the method, an inner cell mass is separated from the host embryo cocultured in the step (iii). The separation of the inner cell mass can be performed using an approach generally known to those skilled in the art. Preferably, the separation of the inner cell mass is performed by a microsurgery method or an immunosurgery method. The microsurgery method is excellent for isolating the inner cell mass while observing the state of the embryo. On the other hand, the immunosurgery (Solter, D. and Knowless, B. B., Proc. Nat. Acad. Sci. USA, 72 (12): 5099-5102 (1975)) causes smaller mechanical damage than that by the microsurgery method and is excellent for isolating the inner cell mass of a blastocyst. Any of these methods may be used.

In the step (v) of the method, the stem cells derived from the first mammalian species-derived pluripotent stem cells or multipotent stem cells are cloned from the inner cell mass obtained in the step (iv) to reestablish stem cells capable of forming chimeras between different species. The cloning of the pluripotent stem cells, etc. from the inner cell mass can be performed using an approach generally known to those skilled in the art. Whether the cloned cells are the stem cells derived from the first mammalian species-derived pluripotent stem cells or multipotent stem cells can be confirmed by labeling the first mammalian species-derived pluripotent stem cells, etc. with an appropriate selective marker before the selection (i.e., before the step (iii)). Alternatively, the host embryo may be labeled with an appropriate selective marker before the step (iii), and cells free from the selective marker can be identified as the first mammalian species-derived pluripotent stem cells or multipotent stem cells and cloned. Examples of the appropriate selective marker include Kusabira Orange (huKO), green fluorescent protein (GFP), Clover, DsRed, mCherry, luciferase, LacZ, neomycin resistance gene, puromycin resistance gene, hygromycin B resistance gene, blasticidin resistance gene, zeocin resistance gene, DT-A gene, and HSV-TK gene. The identification can be performed by identification based on fluorescence, luminescence, staining, etc., or drug selection using a drug resistance gene or the like.

In the case of cloning, for example, pluripotent stem cells, etc. labeled with Kusabira Orange (huKO), this cloning can be performed as follows: blastocysts are removed while observed under a microscope, or the portion concerned is removed by microsurgery. Alternatively, only inner cell masses are isolated by microsurgery or immunosurgery, separately transferred onto feeder cells in 4-well plates, and cultured. From inner cell masses grown after the inoculation, only a morphologically favorable inner cell mass in a mosaic state confirmed to have red fluorescence under a fluorescence microscope is visually selected with proliferative capacity and morphology as indexes and picked up. Also, colonies and cells that morphologically exhibit trophoblast-like cells, epidermoid cells, endoderm-like cells, or the like are removed. The cell mass is dispersed by trypsin treatment and disintegrated into some new cell masses. Then, these cell masses are separately transferred onto newly prepared feeder cells and cultured. From colonies newly formed after the inoculation, a colony in a favorable state confirmed to have red fluorescence under a fluorescence microscope is selected. In subsequent dispersion, the colony is dispersed into cell masses with a smaller number of cells. The step is repeated several times to prepare a colony composed only of pluripotent cells.

In the second embodiment, the present application provides a method for reestablishing stem cells capable of forming chimeras between different species, comprising the following steps:

(i) combining first mammalian species-derived pluripotent stem cells or multipotent stem cells with second mammalian species-derived high-quality pluripotent stem cells to obtain a cell group;

(ii) coculturing the cell group of the step (i) with a second mammalian species-derived host embryo;

(iii) separating an inner cell mass from the host embryo cocultured in the step (ii); and (iv) cloning, from the inner cell mass, stem cells derived from the first mammalian species-derived pluripotent stem cells or multipotent stem cells to reestablish stem cells capable of forming chimeras between different species, wherein the first mammalian species and the second mammalian species are different species, and the first mammalian species-derived pluripotent stem cells or multipotent stem cells are non-rodent mammalian species-derived pluripotent stem cells or multipotent stem cells or are rodent-derived induced pluripotent stem cells (iPS cells) or multipotent stem cells.

In the method of the second embodiment, the steps (i) to (iv) may be repetitively performed. In this case, the step (i) of the 2nd cycle or later is performed by combining the stem cells reestablished in the step (iv) of the preceding cycle with the second mammalian species-derived high-quality pluripotent stem cells to obtain a cell group.

The "pluripotent stem cells or multipotent stem cells", the "high-quality pluripotent stem cells", and the "mammalian species" in the second embodiment can be selected in the same way as in the first embodiment.

In the step (i) of the method of the second embodiment, first mammalian species-derived pluripotent stem cells or multipotent stem cells are combined with second mammalian species-derived high-quality pluripotent stem cells to obtain a cell group. Alternatively, in the case of repeating the steps (i) to (iv) of the second embodiment, in the step (i) of the 2nd cycle or later, the stem cells reestablished in the step (iv) of the preceding cycle are combined with second mammalian species-derived high-quality pluripotent stem cells to obtain a cell group. This step can be performed by every method that can allow the first mammalian species-derived pluripotent stem cells, etc. or the stem cells reestablished in the step (iv) to coexist with the second mammalian species-derived high-quality pluripotent stem cells, or mix therewith the first mammalian species-derived pluripotent stem cells, etc. or the stem cells reestablished in the step (iv).

The steps (ii) to (iv) of the method of the second embodiment correspond to the steps (iii) to (v) of the method of the first embodiment, respectively. The details of each step are as described above.

In a particularly preferred embodiment, the first mammalian species-derived pluripotent stem cells in the method for reestablishing stem cells capable of forming chimeras between different species according to the present application (both of the first and second embodiments) are not human ES cells, and the second mammalian species is not a human.

<Method for Reestablishing Stem Cells Capable of Forming Chimeras Between Same Species>

The present application provides a method for reestablishing stem cells capable of forming chimeras between the same species.

In the first embodiment, the present application provides a method for reestablishing stem cells capable of forming chimeras between the same species, comprising the following steps:

(i) coculturing mammalian species-derived pluripotent stem cells or multipotent stem cells with conspecific mammal-derived high-quality pluripotent stem cells;

(ii) selecting a cell group comprising stem cells that form a cell assembly in the cocultures of the step (i) and are derived from the pluripotent stem cells or the multipotent stem cells;

(iii) coculturing the cell group of the step (ii) with a conspecific mammal-derived host embryo;

(iv) separating an inner cell mass from the host embryo cocultured in the step (iii); and (v) cloning, from the inner cell mass, the stem cells derived from the pluripotent stem cells or the multipotent stem cells to reestablish stem cells capable of forming chimeras between the same species, wherein
the mammalian species-derived pluripotent stem cells or multipotent stem cells are non-rodent mammalian species-derived pluripotent stem cells or multipotent stem cells or are rodent-derived induced pluripotent stem cells (iPS cells) or multipotent stem cells.

The method may further comprise combining the stem cells reestablished in the step (v) with the conspecific mammal-derived high-quality pluripotent stem cells to obtain a cell group, and repeating the steps (iii) to (v). The cell group can be obtained by every method that can allow the stem cells reestablished in the step (v) to coexist with the second mammalian species-derived high-quality pluripotent stem cells, or mix therewith the stem cells reestablished in the step (v).

In the method, the "pluripotent stem cells" are selected from the group consisting of embryonic stem cells (ES cells) and induced pluripotent stem cells (iPS cells). The "multipotent stem cells" are selected from the group consisting of trophoblast stem cells (TS cells), epiblast stem cells (EpiS cells), embryonic germ cells (EG cells), multipotent germline stem cells (mGS cells), nuclear transfer ES cells (ntES cells), hematopoietic stem cells, neural stem cells, and mesenchymal stem cells. In a preferred embodiment, the "pluripotent stem cells or multipotent stem cells" are ES cells or iPS cells. The "high-quality pluripotent stem cells" include ES cells, iPS cells, or an inner cell mass of these cells. The "high-quality pluripotent stem cells" are preferably ES cells.

In the method, the mammalian species is not particularly limited as long as the mammalian species is a mammal. In a preferred embodiment, the mammalian species is selected from the group consisting of a mouse, a rat, a rabbit, a dog, a cat, a horse, cattle, a goat, sheep, a pig, a monkey, and a human and more preferably selected from the group consisting of a mouse, a rat, a pig, a monkey, and a human. Further preferably, the mammalian species is not a human. Thus, the mammalian species can also be selected from the aforementioned group of mammalian species except for the human.

In the step (i) of the method, mammalian species-derived pluripotent stem cells or multipotent stem cells are cocultured with conspecific mammal-derived high-quality pluripotent stem cells. In the step, the coculture is performed in vitro under conditions suitable for the culture of the high-quality pluripotent stem cells, conditions suitable for the culture of naive pluripotent stem cells, or combined conditions thereof. Those skilled in the art can appropriately set the type of a medium and culture conditions such as culture temperature and culture time, suitable for the culture.

Preferred examples of the culture conditions include conditions involving gas concentrations of 5% $CO_2$ and 95% air and a culture temperature of 37° C. to 39° C. For example, iPS cells labeled with a selective marker are mixed with conspecific high-quality pluripotent stem cells to prepare cell masses. The cell masses are inoculated to dishes coated with feeder cells. MEF (mouse embryonic fibroblast) can be used as the feeder cells. Colonies in a favorable mosaic state are collected by selection using various selective markers such as fluorescent proteins and visual selection of morphology favorable for cloning. After further inoculation of the colonies, a colony in a good state having the selective marker such as fluorescence is selected from newly formed colonies. In this respect, the medium conditions are, for example, such optimum conditions that the culture is first performed under high-quality pluripotent stem cell medium conditions, which are gradually changed to naive pluripotent stem cell culture conditions. For example, the "medium composition for naive pig iPS cells" or the "medium composition for mouse ES cells" given in the description about the step (i) of the method of the first embodiment in the paragraph "Method for reestablishing pluripotent stem cells or multipotent stem cells capable of forming chimeras between different species" may be used.

In the step (ii) of the method, a cell group comprising stem cells that form a cell assembly in the cocultures of the step (i) and are derived from the pluripotent stem cells or the multipotent stem cells is selected. The step (ii) can be performed according to and in the same way as in the description about the step (ii) of the method of the first embodiment in the paragraph "Method for reestablishing pluripotent stem cells or multipotent stem cells capable of forming chimeras between different species".

In the step (iii) of the method, the cell group of the step (ii) is cocultured with a conspecific mammal-derived host embryo. A conspecific chimeric embryo is prepared by the coculture of the cell group of the step (ii) with the conspecific mammal-derived host embryo. In the coculture of the step (iii), the conspecific chimeric embryo is then cultured until an early blastocyst stage where an inner cell mass (ICM) is obtained. In a preferred embodiment, the coculture of this step is performed by microinjecting or aggregating the cell group of the step (ii) to the conspecific mammal-derived host embryo, followed by coculture.

In the method, the host embryo can be selected according to and in the same way as in the description in the paragraph "Method for reestablishing pluripotent stem cells or multipotent stem cells capable of forming chimeras between different species".

Preferably, the step (iii) of the method is performed by microinjecting or aggregating the cell group of the step (ii) to the conspecific mammal-derived early embryo or tetraploid embryo, followed by coculture. More preferably, the step (iii) of the method is performed by microinjecting the cell group of the step (ii) to the conspecific mammal-derived early embryo or tetraploid embryo, followed by coculture.

In the step (iv) of the method, an inner cell mass is separated from the host embryo cocultured in the step (iii). In the step (v), the stem cells derived from the pluripotent stem cells or the multipotent stem cells are cloned from the inner cell mass to reestablish stem cells capable of forming chimeras between the same species. The steps (iv) and (v) of the method can be performed according to and in the same way as in the description about the steps (iv) and (v) in the method of the first embodiment in the paragraph "Method for reestablishing pluripotent stem cells or multipotent stem cells capable of forming chimeras between different species".

In the second embodiment, the present application provides a method for reestablishing stem cells capable of forming chimeras between the same species, comprising the following steps:

(i) combining mammalian species-derived pluripotent stem cells or multipotent stem cells with conspecific mammal-derived high-quality pluripotent stem cells to obtain a cell group;

(ii) coculturing the cell group of the step (i) with a conspecific mammal-derived host embryo;

(iii) separating an inner cell mass from the host embryo cocultured in the step (ii); and (iv) cloning, from the inner cell mass, stem cells derived from the pluripotent stem cells or the multipotent stem cells to reestablish stem cells capable of forming chimeras between the same species, wherein the mammalian species-derived pluripotent stem cells or multipotent stem cells are non-rodent mammalian species-derived pluripotent stem cells or multipotent stem cells or are rodent-derived induced pluripotent stem cells (iPS cells) or multipotent stem cells.

In the method of the second embodiment, the steps (i) to (iv) may be repetitively performed. In this case, the step (i) of the 2nd cycle or later is performed by combining the stem cells reestablished in the step (iv) of the preceding cycle with the conspecific mammal-derived high-quality pluripotent stem cells to obtain a cell group.

The "pluripotent stem cells or multipotent stem cells", the "high-quality pluripotent stem cells", and the "mammalian species" in the second embodiment can be selected in the same way as in the first embodiment.

In the step (i) of the method of the second embodiment, mammalian species-derived pluripotent stem cells or multipotent stem cells are combined with conspecific mammal-derived high-quality pluripotent stem cells to obtain a cell group. Alternatively, in the case of repeating the steps (i) to (iv) of the second embodiment, in the step (i) of the 2nd cycle or later, the stem cells reestablished in the step (iv) of the preceding cycle are combined with conspecific mammal-derived high-quality pluripotent stem cells to obtain a cell group. This step can be performed by every method that can allow the mammalian species-derived pluripotent stem cells, etc. to coexist with the conspecific mammal-derived high-quality pluripotent stem cells, or mix therewith the mammalian species-derived pluripotent stem cells, etc.

The steps (ii) to (iv) of the method of the second embodiment correspond to the steps (iii) to (v) of the method of the first embodiment, respectively. The details of each step are as described above.

<Pluripotent Stem Cells or Multipotent Stem Cells Capable of Forming Chimeras>

The present application provides stem cells capable of forming chimeras, obtained by any of the reestablishment methods described above.

The stem cells of the present invention are stem cells reestablished from non-rodent mammalian species-derived pluripotent stem cells or multipotent stem cells, or from rodent-derived iPS cells or multipotent stem cells, and have one or more features selected from the group consisting of the following:

being capable of forming chimeras;

being capable of forming a cell assembly; and having high affinity for the niche environment of an inner cell mass.

The method for reestablishing stem cells capable of forming chimeras according to the present invention selects pluripotent stem cells, etc. on the basis of whether or not the pluripotent stem cells, etc. form a colony (i.e., contribute to colony formation) together with ES cells and/or on the basis of whether or not the pluripotent stem cells, etc. constitute a portion of an inner cell mass (i.e., contribute to ICM). Accordingly, the stem cells reestablished by the method of the present invention have the features described above. The stem cells capable of forming chimeras, reestablished by the method of the present invention are cells refined and reestablished as a transplantable line by removing cells incapable of forming chimeras, which have coexisted with pluripotent stem cells, etc. before the reestablishment.

As shown in Examples 6 to 9, the stem cells reestablished by the method of the present invention have the property of having the higher expression of naive pluripotent and core pluripotent gene groups, i.e., maintain a more undifferentiated state, as compared with cells before the reestablishment. This means having excellent properties as stem cells capable of forming chimeras.

The stem cells capable of forming chimeras, reestablished by the method of the present invention can be used for purposes given below without particular limitation.

A chimeric animal can be prepared by the blastocyst complementation method using the stem cells capable of forming chimeras according to the present invention to form an organ or an organ anlage derived from the stem cells. Such an organ or an organ anlage is useful in regenerative medicine.

Also, a chimeric embryo or a chimeric fetus can be prepared by the blastocyst complementation method using the stem cells capable of forming chimeras according to the present invention to obtain somatic stem cells, organ progenitor cells, and somatic cells derived from the chimeric embryo or the chimeric fetus. Furthermore, the somatic stem cells derived from the chimeric embryo or the chimeric fetus can also be differentiated in vitro to obtain organ progenitor cells and somatic cells. Alternatively, the stem cells capable of forming chimeras according to the present invention can also be differentiated in vitro to obtain somatic stem cells, organ progenitor cells, and somatic cells. These somatic stem cells, organ progenitor cells, and somatic cells are useful for use in drug efficacy evaluation or pathological analysis. Since the stem cells capable of forming chimeras according to the present invention are high-quality stem cells that maintain the capability of forming chimeras, the cells can be used as a starting cells for efficient preparation of or differentiation into a chimeric embryo or a chimeric animal.

Alternatively, the stem cells capable of forming chimeras according to the present invention can be used in a tetraploid rescue method to prepare an animal harboring the propagated stem cells. The tetraploid rescue method is a method based on the mechanism under which iPS or ES cells, etc. are injected to tetraploid fertilized eggs so that tetraploid cells develop into placentae while only the iPS or ES cells, etc. develop into individuals (Nagy, A., et al., Development, 110, 815-821 (1990)). Such an animal preparation method is effective for the preservation, regeneration, and/or maintenance of rare species of animals such as endangered species, companion mammals such as pet animals, or useful commercial animals. In this case, pluripotent stem cells, etc.

capable of forming chimeras between the same species are desirably used as the pluripotent stem cells, etc. capable of forming chimeras according to the present invention.

<Method for Conducting Drug Efficacy Evaluation or Pathological Analysis Using Cells>

The present application provides a method for conducting drug efficacy evaluation or pathological analysis using stem cells capable of forming chimeras, obtained by any of the reestablishment methods described above, or somatic stem cells, organ progenitor cells, or somatic cells obtained by the differentiation of the stem cells capable of forming chimeras. Specifically, the present application provides a method for conducting drug efficacy evaluation or pathological analysis using cells, comprising the following steps:

(i) obtaining cells, wherein the cells are (A) stem cells capable of forming chimeras, reestablished by the method of the present invention or (B) somatic stem cells, organ progenitor cells, or somatic cells obtained by the differentiation of stem cells capable of forming chimeras, reestablished by the method of the present invention, wherein the somatic stem cells, the organ progenitor cells, or the somatic cells are obtained by any of the following methods (a) to (c):

(a) preparing a chimeric embryo or a chimeric fetus from the stem cells capable of forming chimeras, reestablished by the method of the present invention, and obtaining somatic stem cells, organ progenitor cells, or somatic cells derived from the chimeric embryo or the chimeric fetus;

(b) differentiating in vitro the somatic stem cells derived from the chimeric embryo or the chimeric fetus obtained in method (a) to obtain organ progenitor cells or somatic cells; and (c) differentiating in vitro the stem cells capable of forming chimeras, reestablished by the method of the present invention to obtain somatic stem cells, organ progenitor cells, or somatic cells; and (ii) conducting drug efficacy evaluation or pathological analysis using the cells obtained in the step (i).

In the step (i) of the method, the "stem cells capable of forming chimeras" of (A) can be obtained by reestablishment from pluripotent stem cells or multipotent stem cells by any of the methods described in the "method for reestablishing stem cells capable of forming chimeras between different species" and the "method for reestablishing stem cells capable of forming chimeras between the same species".

In the step (i) of the method, the "somatic stem cells, organ progenitor cells, or somatic cells obtained by the differentiation of the stem cells capable of forming chimeras" of (B) can be obtained by first obtaining the "stem cells capable of forming chimeras" in the same way as in (A) and then performing any of the following methods (a) to (c).

Method (a) comprises preparing a chimeric embryo or a chimeric fetus from the stem cells capable of forming chimeras, and obtaining somatic stem cells, organ progenitor cells, or somatic cells derived from the chimeric embryo or the chimeric fetus. The method for preparing the chimeric embryo or the chimeric fetus can be performed by the method described about the preparation of a chimeric embryo or a chimeric animal in the paragraph "Definition". In order to obtain the somatic stem cells, the organ progenitor cells, or the somatic cells from the chimeric embryo or the chimeric fetus, the cells are separated and established. The separation and establishment of the somatic stem cells, the organ progenitor cells, or the somatic cells from the chimeric embryo or the chimeric fetus can be appropriately performed by a method usually used by those skilled in the art.

Method (b) comprises differentiating in vitro the somatic stem cells derived from the chimeric embryo or the chimeric fetus obtained in method (a) to obtain organ progenitor cells or somatic cells. The method for differentiating in vitro the somatic stem cells to obtain organ progenitor cells or somatic cells can be appropriately performed by a method usually used by those skilled in the art.

Method (c) comprises differentiating in vitro the stem cells capable of forming chimeras to obtain somatic stem cells, organ progenitor cells, or somatic cells. The method for differentiating in vitro the stem cells capable of forming chimeras to obtain somatic stem cells, organ progenitor cells, or somatic cells can be appropriately performed by a method usually used by those skilled in the art for differentiating pluripotent stem cells in vitro.

The "somatic stem cells, organ progenitor cells, or somatic cells" obtained in the step (i) of the method are, for example, cells associated with the heart, the nerve, the kidney, the liver, the pancreas, skeletal muscle, cells of hematopoietic lineage, or the like, but are not particularly limited.

In the step (ii) of the method, drug efficacy evaluation or pathological analysis is conducted using the cells obtained in the step (i). The drug efficacy evaluation or the pathological analysis may be a testing method using the cells and can be appropriately conducted by a method usually used by those skilled in the art.

EXAMPLES

Hereinafter, specific examples of the present invention will be described. These specific examples are provided for illustrative purposes for understanding the present invention and are not intended to limit the scope of the present invention.

Example 1: Reestablishment of iPS Cells Capable of Forming Chimeras Between Different Species Pig iPS cells transfected with red fluorescent protein (Kusabira Orange, huKO) were cocultured with mouse ES cells, and colonies having favorable proliferative capacity and morphology were selected. The pig iPS cells were microinjected to 45 mouse tetraploid blastocysts (F1×B6) and then cocultured for 1 day under mouse early embryo culture conditions (mwm culture solution, 5% $CO_2$, 37° C.). Blastocysts having an abnormal shape or harboring naive pig iPS cells residing in areas other than ICM were removed under a microscope, and only favorable embryos were separately transferred onto feeder cells in 4-well plates and cultured. From ICM grown after the inoculation, only a morphologically favorable inner cell mass in a mosaic state confirmed to have red fluorescence under a fluorescence microscope (Axio Observer D1 system, Carl Zeiss AG) was visually selected with proliferative capacity and morphology as indexes and picked up. The cell mass was dispersed by treatment with 0.025% trypsin/0.1 mM EDTA, and the resulting cell masses were separately transferred onto newly prepared feeder cells in 4-well plates and cultured. From colonies further newly formed after the inoculation, colonies in a favorable state confirmed to have red fluorescence under a fluorescence microscope were selected (4 lines). These colonies were used as colonies after reestablishment (FIG. 2).

Example 2: Study on Karyotype of Reestablished iPS Cells

Figure 3:
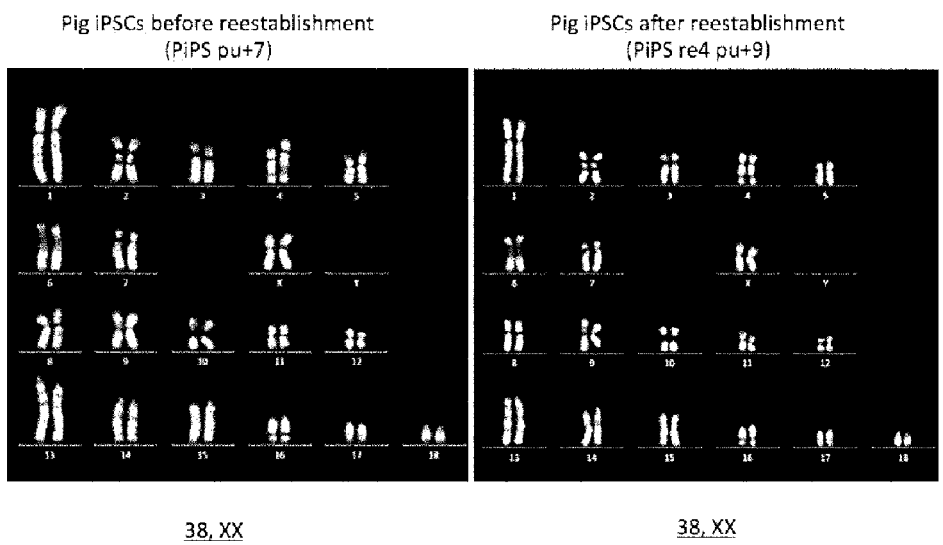
FIG. 3 shows results of studying the karyotypes of pig iPS cells after reestablishment by a Q-band staining method. These cells had a normal karyotype (38, XX) both before selection and after reestablishment.

The pig iPS cells before reestablishment and the iPS cells after reestablishment were studied for their karyotypes by the Q-band staining method. As a result, these cells had a normal karyotype (38, XX) in both cases. Thus, the operation of reestablishment did not cause any change in karyotype caused by cell fusion, chromosome elimination, etc. This indicated that the operation of reestablishment was based on cloning from the heterogeneous iPS cell population (FIG. 3).

Example 3: Chimeric Animal Preparation Using Reestablished iPS Cells

The reestablished pig iPS cells were studied for their capability of forming chimeras, by transfer to mouse blastocysts. For transplantation, approximately 10 pig iPS cells after reestablishment were injected per blastocyst-stage embryo (F1×B6, etc.) using a piezo micromanipulator. The blastocyst-stage embryos thus receiving the injection were transplanted to the uteri of 8 recipient ICR mice 2.5 or 3.5 days after confirmation of their vaginal plugs. On 8.5, 9.5, or 10.5 days of pregnancy, the recipient ICR mice were euthanized by cervical dislocation. Then, the uteri were taken out to collect embryonic placentae together with decidual membranes. At E9.5, E10.5, and E11.5, a plurality of interspecific chimeric mice and amnions were able to be collected. Red fluorescence from the pig iPS cell-derived cells that formed the chimeras was confirmed under a fluorescence stereomicroscope (M165 FC, Leica Microsystems GmbH) (FIG. 4). As a result, the pig iPS cell-derived cells were confirmed to be present in the embryos, indicating that chimeric animals can be prepared using reestablished iPS cells. Also, the pig iPS cell-derived cells were also found to be present in the amnions (embryo-derived tissues). No red fluorescence was confirmed in a negative control (normal mouse placenta).

Example 4: Preparation of Chimeric Animal Using Reestablished iPS Cells

In order to confirm the presence of pig iPS cells in chimeric embryos, an attempt was made to detect pig mitochondrial DNA (mtDNA) from E9.5 and E10.5 embryos and amnions by PCR.

Specifically, the E9.5 and E10.5 chimeric embryos and amnions observed under a fluorescence stereomicroscope were treated with protease, followed by the extraction of their respective DNAs. These DNAs were used in PCR to detect pig mtDNA and mouse mtDNA. For the detection of the pig mtDNA, 40 cycles each involving 94° C. for 15 seconds, 62° C. for 20 seconds, and 72° C. for 40 seconds were carried out using a primer set of 5'-CAT TGG AGT AGT CCT ACT ATT TAC CGT T-3' (SEQ ID NO: 1) and 5'-GGA TTA GTA GGA TTA GTA TTA TAA ATA AGG CTC-3' (SEQ ID NO: 2) and rTaq. For the detection of the mouse mtDNA, 35 cycles each involving 94° C. for 30 seconds, 55° C. for 30 seconds, and 72° C. for 30 seconds were carried out using a primer set of 5'-ATC ATT CAT AGC CTG GCA GA-3' (SEQ ID NO: 3) and 5'-AAG GAT GAA TAT GGA TTT GC-3' (SEQ ID NO: 4) and rTaq. The PCR specificity was high, and, as indicated by pig fibroblasts and a B6 mouse tail DNA control, each primer set detected only the pig or mouse mtDNA. The pig iPS cells were cultured on mouse feeder cells and therefore detected by both the primer sets (FIG. 5).

Figure 5:
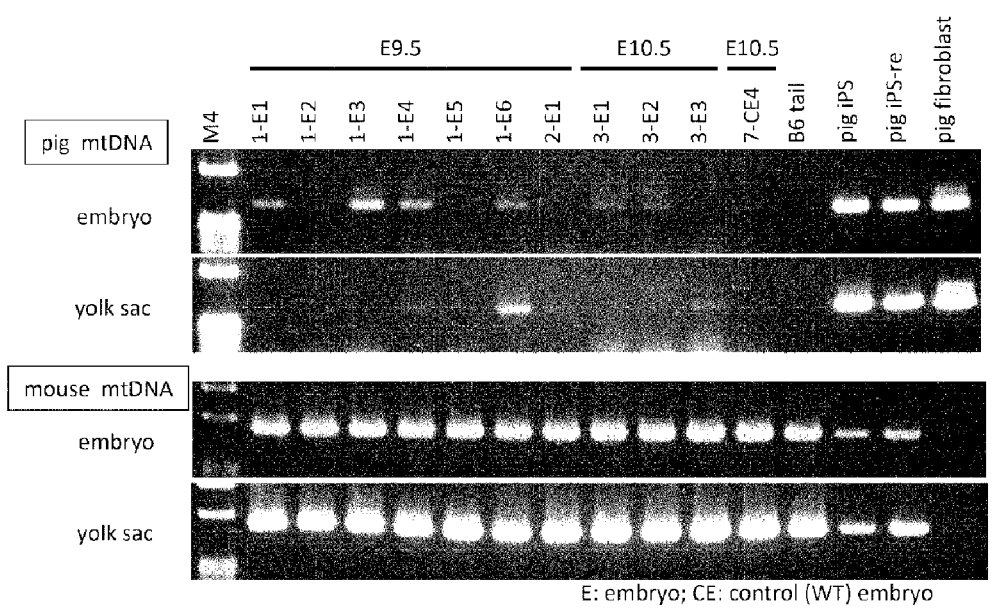
FIG. 5 is a photograph showing results of detecting pig and mouse mitochondrial DNAs (mtDNAs) in order to confirm the presence of pig iPS cells in chimeric embryos and amnions.

The pig mtDNA was detected at a rate of 6/10 in the embryos and at a rate of 5/10 in the amnions (yolk sacs) (FIG. 5). In short, interspecific chimeric embryos were formed with high frequency, indicating that the reestablished pluripotent stem cells are very highly capable of forming chimeras. In addition, the present cells also exhibited differentiation capacity into amnions, indicating that these cells acquired a high level of pluripotency.

Example 5: Reestablishment of iPS Cells Capable of Forming Chimeras Between Same Species Favorable colonies were isolated by reestablishment from mouse iPS cells. Chimeric mice were prepared using these colonies and blastocysts of male sterile mice, and testes and sperms were prepared by the complementation method.

Specifically, male C57BL/6J-Tg (EGPF)-derived iPS cells hardly capable of forming chimeras were reestablished by the method of Example 1 to obtain reestablished iPS cells. Next, superovulation was induced in 3-week-old C57BL/6J female mice by hormone treatment. Then, the female mice were mated with sympatric mouse SPR2 (*Mus spretus*) male mice to obtain many fertilized embryos (interspecific hybrid embryos). Approximately 10 reestablished iPS cells were injected per interspecific hybrid blastocyst using a piezo micromanipulator. 30 blastocyst-stage embryos thus receiving the injection were transplanted to the uterus of one recipient ICR mouse 2.5 days after confirmation of its vaginal plug. On the evening before delivery (evening of 18.5 days of pregnancy), 3 male embryos were taken out by cesarean section. All of the embryos were confirmed to have iPS cell-derived cells in their testes by the detection of green fluorescence using a fluorescence microscope (FIG. 6).

Example 6: Hierarchical Clustering of Gene Expression Profiles in Cells Before and After Reestablishment RNA was extracted from each of 3 dishes for the culture of the pig iPS cells before reestablishment (iPS cell) and 3 dishes for the culture of the pig iPS cells after reestablishment (Re-iPS cell).

TABLE 1

|  | Sample ID | RG Sample ID |
| --- | --- | --- |
| Re-iPS cell | piPS1 | TR_2160_019 |
| Re-iPS cell | piPS5 | TR_2160_023 |
| Re-iPS cell | piPS6 | TR_2160_024 |
| iPS cell | piPS3 | TR_2160_021 |
| iPS cell | piPS8 | TR_2160_030 |
| iPS cell | piPS9 | TR_2160_031 |

The respective RNAs extracted from the cells were subjected to RNA-Seq using HiSeq 2000 (Illumina, Inc.) and mapped using pig transcriptome pipeline. As a result, 17,092 genes were identified. The expression levels of the genes assayed by the combination of comparisons between samples were indicated by FPKM (fragments per kilobase of exon per million mapped fragments) values and clustered by the group average method, and the distances were measured using the Canberra algorithm.

Figure 7:
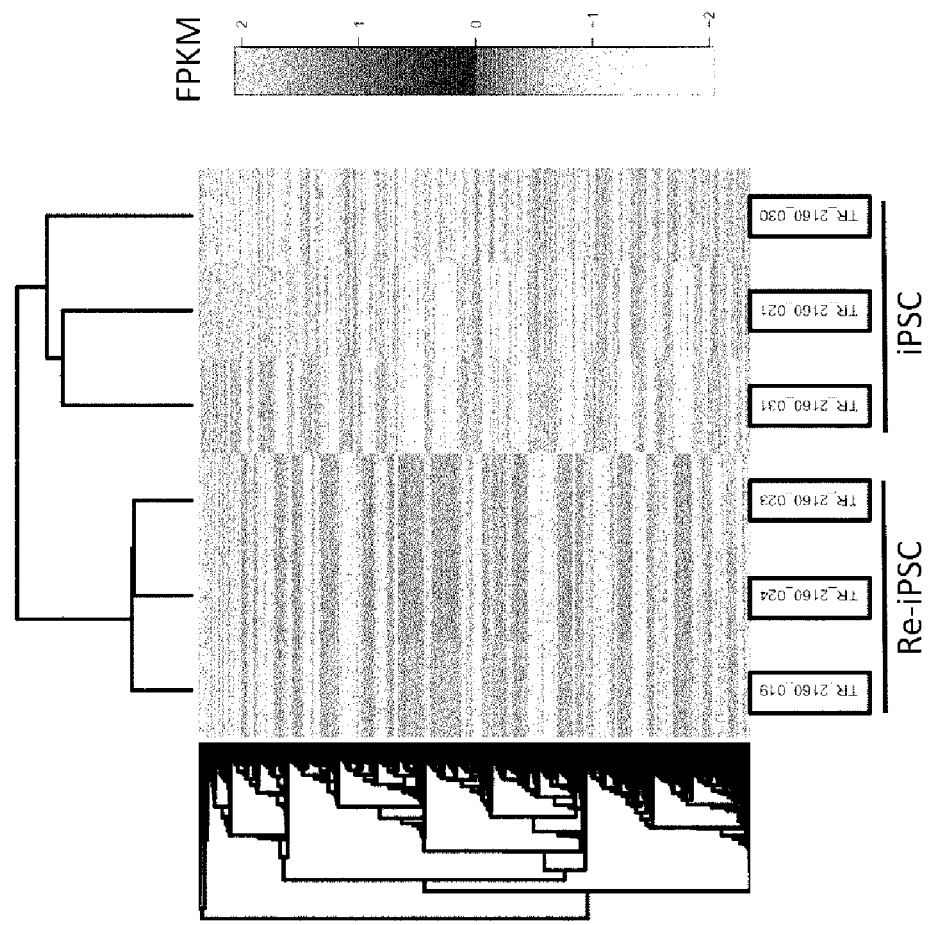
FIG. 7 is a diagram showing results of the hierarchical clustering of gene expression profiles in pig iPS cells before reestablishment and after reestablishment.

The results of the hierarchical clustering of gene expression profiles in the pig iPS cells before reestablishment and after reestablishment are shown in FIG. 7. The respective gene expression profiles of the cells before reestablishment and the cells after reestablishment were broadly divided into two groups. Specifically, it was revealed that the gene expression profile of the cells after reestablishment is different from that of the cells before reestablishment and exhibits particular gene expression patterns.

Example 7: Expression of Four Yamanaka Factors in Reestablished iPS Cells (1) Expression Levels of Endogenous Genes The iPS cells before reestablishment (piPS3, piPS8, and piPS9) and the iPS cells after reestablishment (piPS1, piPS5, and piPS6) obtained in Example 6 were studied for change in the gene expression levels of pig endogenous genes (PAU5F1 (Oct4), KLF4, SOX2, and MYC) corresponding to four Yamanaka factors, and NANOG gene important for pluripotency maintenance, between before and after reestablishment on the basis of change in FPKM value. The results are shown in FIG. 8. The gene expression levels of NANOG, PAU5F1 (Oct4), and KLF4 necessary for pluripotency maintenance were significantly elevated ($\log_2$ value of the FPKM value: 1.3 or more). By contrast, the expression level of SOX2 was not changed, and the expression level of MYC tended to be decreased, albeit with no significant difference. From these results, the elevated expression of the endogenous genes important for pluripotency maintenance was found in the pig iPS cells after reestablishment.

(2) Expression Levels of Exogenous Genes

The pig iPS cells used in this Example are originally prepared by transferring genes of human four Yamanaka factors to pig fibroblasts. In general, the gene expression of foreign genes of four Yamanaka factors transferred at the time of iPS cell preparation tends to be suppressed in naive mouse iPS cells, etc. In Example 7(2), foreign genes of human four Yamanaka factors transferred at the time of iPS cell preparation were studied for change in their gene expression between before and after reestablishment.

The RNA-Seq results of Example 6 were mapped to human genes using human transcriptome pipeline to identify human gene-derived transcripts. As a result, the rate of mapping to human genes was 3 to 4%, and the ratio to human genes was proper. Study on the expression of human four Yamanaka factors genes (hPAU5F1 (hOct4), hKLF4, hSOX2, and hMYC) before and after reestablishment revealed that the expression of all of these genes was significantly decreased. A human NANOG gene (hNANOG), which is not included in the four Yamanaka factors, was studied as a negative control. Its expression was hardly detectable both before and after reestablishment (negative control). From these results, the expression of the human four Yamanaka factors transferred for the pig iPS cell establishment was significantly decreased after reestablishment.

FIG. 10 summarizes the tendency of change in gene expression in the paragraphs (1) (FIG. 8) and (2) (FIG. 9). It was revealed that: the gene expression of the foreign four Yamanaka factors was suppressed in the cells after reestablishment; and the gene expression of endogenous NANOG, Oct4 (PAU5F1), and KLF4 important for pluripotency maintenance was increased. The cells after reestablishment had a naive tendency as described above.

Example 8: Pearson Correlation Analysis of Reestablished Cells

In Example 6, the iPS cells before reestablishment (piPS3, piPS8, and piPS9) and the iPS cells after reestablishment (piPS1, piPS5, and piPS6) were subjected to RNA-Seq, and the results were mapped using pig transcriptome pipeline. Pearson correlation coefficients were yielded as to their respective gene expression profiles to study the similarity between their expression profiles.

Figure 11:
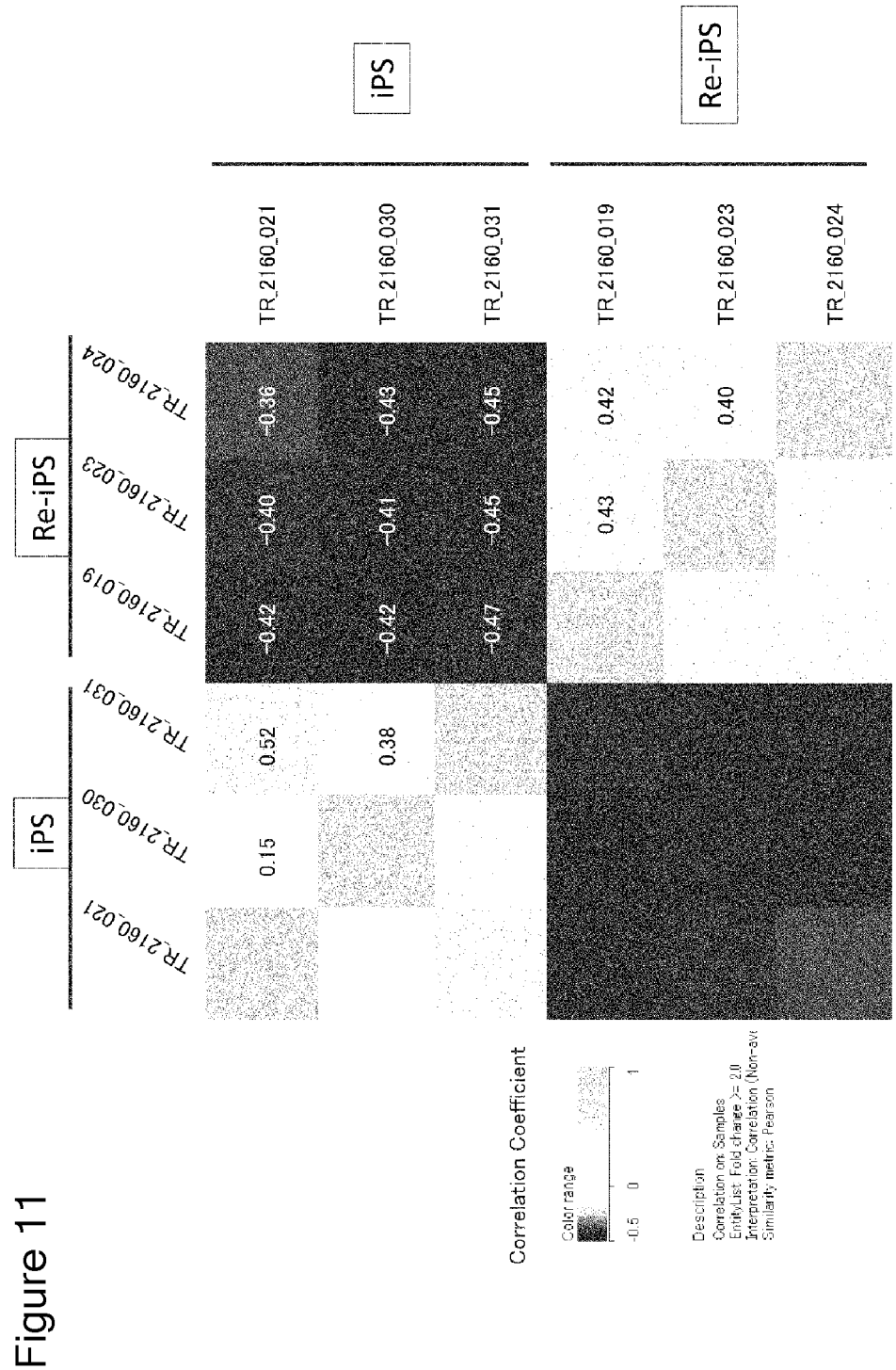
FIG. 11 is a diagram showing results of the Pearson correlation analysis of gene expression profiles in cells before and after reestablishment.

The results are shown in FIG. 11. No variation in profile among the cells (dishes) was found in the cell group after reestablishment (Re-iPS cell). By contrast, large variation in gene expression profile among the cells (dishes) was found in the cells before reestablishment (iPS cell). From these results, diverse cells were found to coexist in the iPS cells before reestablishment, resulting in large variation among the culture dishes, whereas the reestablished cells exhibited no variation even after culture and had homogeneous properties. It was revealed that the technique for reestablishment selects only clones having homogeneous properties, which are not largely changed even by subsequent culture.

Example 9: Gene Ontology (GO) Analysis Using DAVID

From the RNA-Seq results obtained in Example 6, a gene group whose expression levels in the iPS cells after reestablishment (piPS1, piPS5, and piPS6) were changed by 2 or more in terms of a $\log_2$ value as compared with the cells before reestablishment (piPS3, piPS8, and piPS9) was extracted and subjected to gene ontology (GO) analysis using Database for Annotation, Visualization and Integrated Discovery (DAVID) (provided by National Institute of Allergy and Infectious Diseases (NIAID), NIH).

FIG. 12 is a diagram summarizing, as a result of the GO analysis, the types of genes whose expression in the reestablished cells was increased by 2 or more in terms of a $\log_2$ value as compared with the cells before reestablishment, and the types of genes whose expression in the reestablished cells was decreased as compared with the cells before reestablishment. The expression of genes involved in glycoproteins, cell adhesion molecules, embryonic morphogenesis, extracellular matrix, etc. was increased in the reestablished cells.

In Nature Cell Biology, 16: 513 (2014), stages from two-cell mouse embryos to differentiation and growth into blastocysts after transplantation were divided into E1.5 to E5.5 stages, and gene expression levels at each stage were examined. As a result, the property of each gene expression was grouped as 4 types: naive pluripotency, core pluripotency, primed pluripotency, and primitive endoderm.

Figure 13:
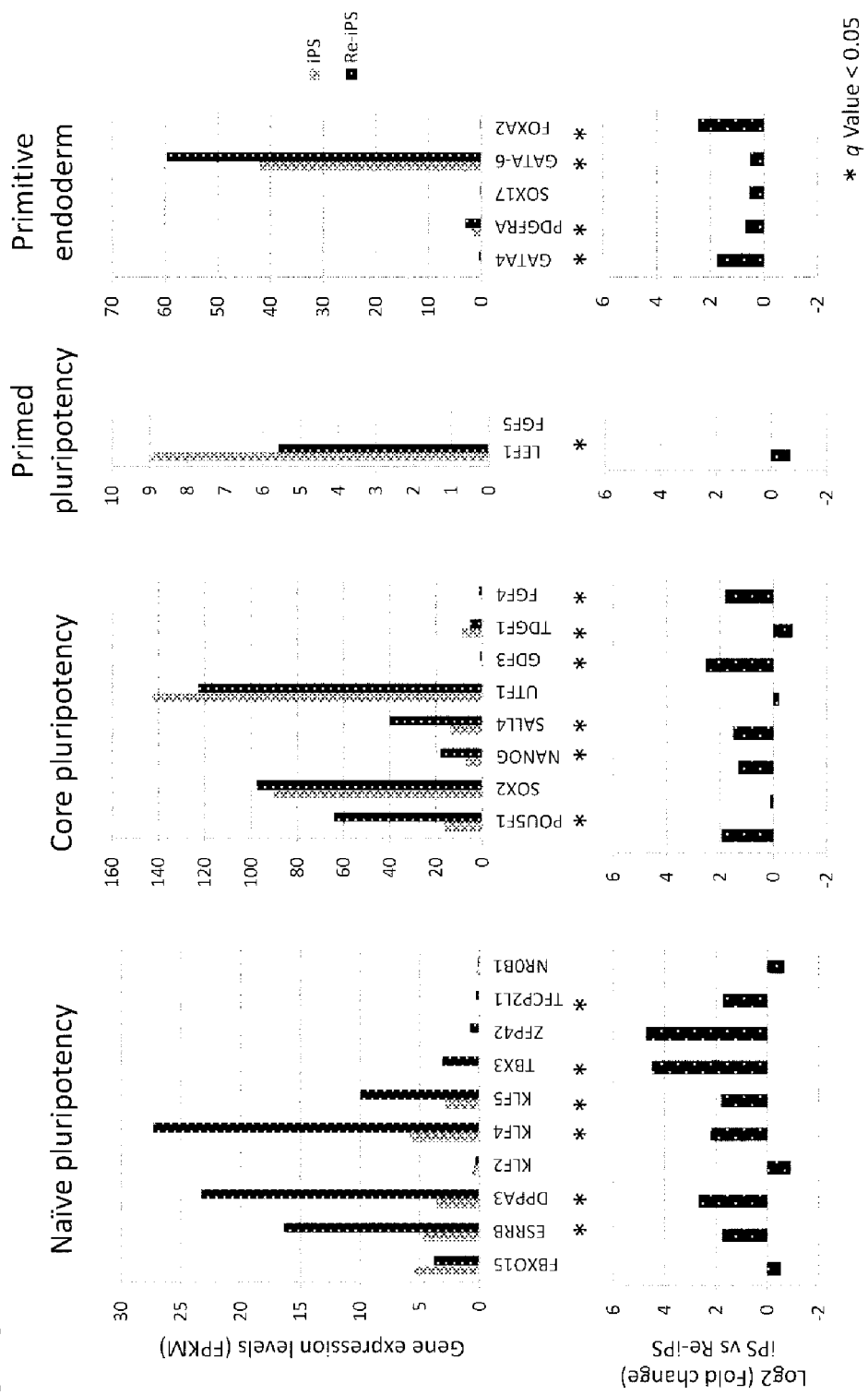
FIG. 13 is a diagram showing that the expression of a gene associated with each of properties of naive pluripotency, core pluripotency, primed pluripotency, and primitive endoderm was compared between before and after reestablishment of pig iPS cells. Upper graphs: FPKM value of each gene; and lower graphs: $\log_2$ value of change in gene expression level between before and after reestablishment.

FIG. 13 is a diagram showing that the expression of genes associated with each of properties of naive pluripotency, core pluripotency, primed pluripotency, and primitive endoderm was compared between before and after reestablishment of pig iPS cells. The upper graphs depict the FPKM value of each gene. The lower graphs depict the $\log_2$ value of change in gene expression level between before and after reestablishment. The reestablishment increased the expression levels of genes associated with the property of naive pluripotency, such as Tbx3, ESRRB, DPPA3, and KLF4, and genes associated with the property of core pluripotency, such as POU5F1, NANOG, SALL4, and GDF3. On the other hand, the expression level of LEF1 associated with the property of primed pluripotency was decreased. It should be understood that the reestablishment rendered the iPS cells naiver.

Figure 14:
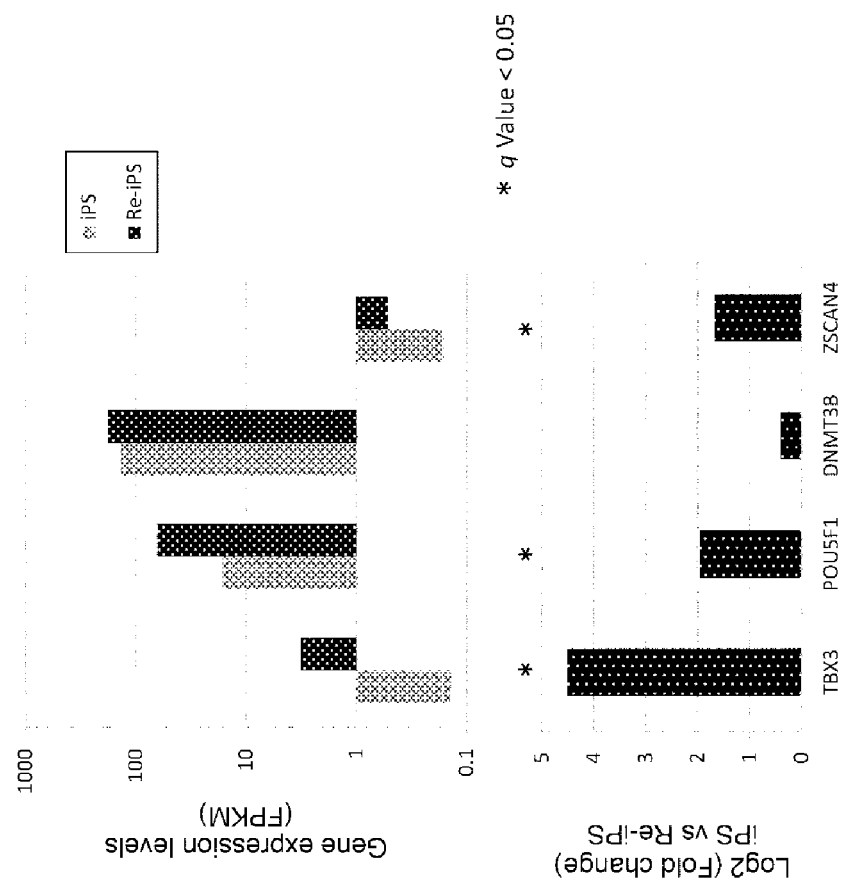
FIG. 14 is a diagram showing that the expression of each of Tbx3, Pou5F1 (Oct4), and Zscan4 genes was compared between before and after reestablishment of pig iPS cells. Upper graphs: FPKM value of each gene; and lower graphs: $\log_2$ value of change in gene expression level between before and after reestablishment.

Scientific Rep. 3: 3492 (2013) states that Tbx3 and Zscan4 are involved in the control of two-cell mouse embryos (control of an undifferentiated state). FIG. 14 shows that the expression of each of Tbx3, Pou5F1 (Oct4), and Zscan4 genes was increased in the pig iPS cells by reestablishment. Zscan4 is known as a gene involved in the telomerase-independent maintenance of telomere and the stability of the genome, and can be used as a marker for the undifferentiated state of cells. It was revealed that, in reestablished iPS cells, Zscan4 is increased, and a two-cell state (undifferentiated state) is maintained.

Nature Cell Biology, 16: 513 (2014) illustrates the details of constituents of the embryonic extracellular matrix of a mouse blastocyst. The embryonic extracellular matrix constituents include integrins, laminins, ICAM, collagens, etc. Particularly, fibronectin Fn1, laminin a5, laminin b1, and laminin c1 chains occupy 40% or more.

Figure 15:
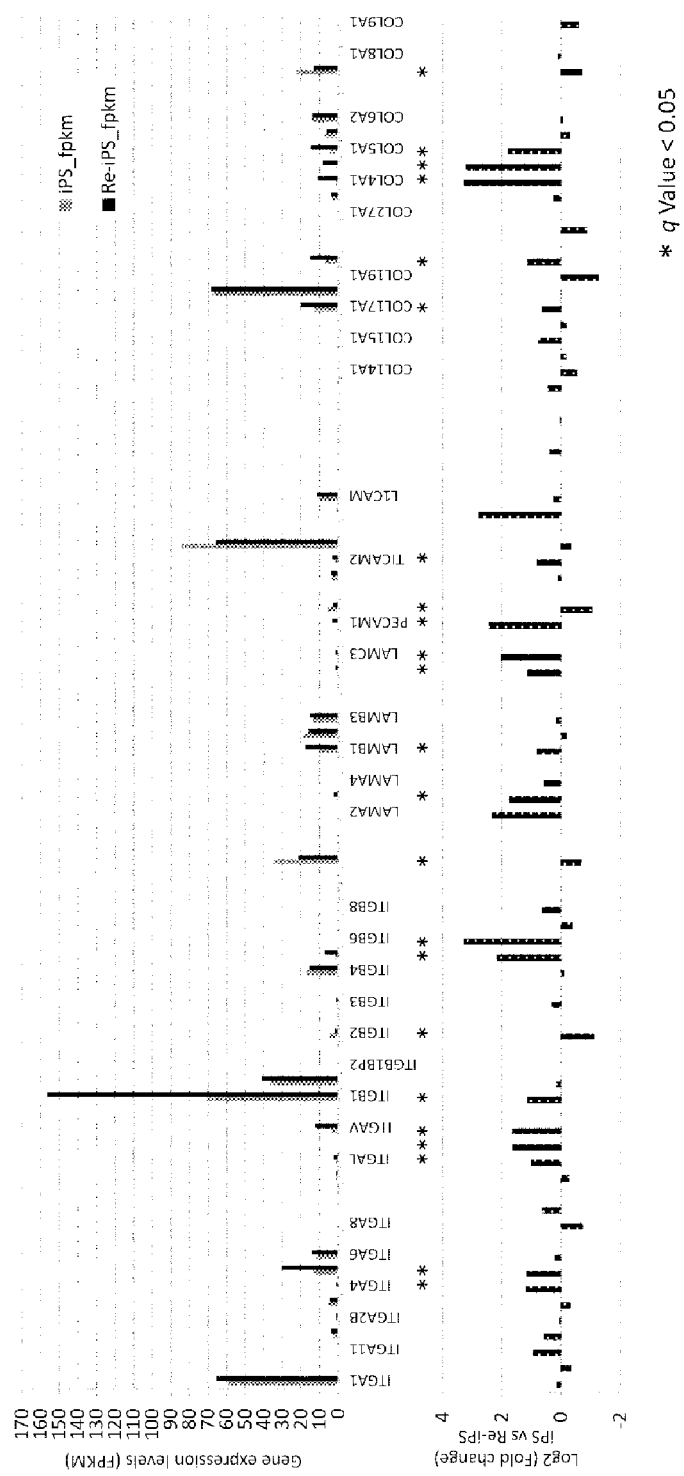
FIG. 15 is a diagram showing that the expression of each gene of a constituent of embryonic extracellular matrix was compared between before and after reestablishment of pig iPS cells.

FIG. 15 is a diagram showing that the expression of each gene of a constituent of embryonic extracellular matrix was compared between before and after reestablishment of pig iPS cells. The upper graphs depict the FPKM value of each gene. The lower graphs depict the $\log_2$ value of change in gene expression level between before and after reestablishment. The reestablishment increased the expression of many extracellular matrix genes, such as plural types of integrins, laminins, ICAM, and collagens.

INDUSTRIAL APPLICABILITY

According to the method of the present invention, a cell group capable of forming chimeras can be acclimatized and selected from a heterogeneous cell group of pluripotent stem cells, etc. prepared by an existing method. Specifically, the method of the present invention is a technique for monocloning the heterogeneous cell population to obtain high-quality stem cells. This technique is useful for obtaining starting cells for organ formation using iPS cells or ES cells, etc. in regenerative medicine. The method of the present invention does not compete with any existing method for establishing pluripotent stem cells, etc. The method of the present invention is carried out after implementation of the existing method and thereby contributes to obtainment of higher-quality pluripotent stem cells, etc. and enhancement in the success rate of organ formation, etc. In addition, cells reestablished by the method of the present invention, somatic cells, somatic stem cells, and organ progenitor cells obtained from a chimeric embryo or fetus prepared from the cells reestablished by the method of the present invention, and somatic stem cells, organ progenitor cells, and somatic cells obtained by the in vitro differentiation of the cells reestablished by the method of the present invention are useful in pathological analysis, drug efficacy evaluation, or the like.

Alternatively, the provision of the pluripotent stem cells, etc. capable of forming chimeras is also useful in the preservation, regeneration, and/or maintenance of rare species of animals such as endangered species, companion mammals such as pet animals, and useful commercial animals.

The invention claimed is:

1. A method for establishing stem cells capable of forming chimeras between different or conspecific species, comprising the following steps:

(A)
  (i) coculturing pluripotent stem cells or multipotent stem cells from a first mammalian species (PSC1s or MSC1s) with nave pluripotent stem cells from a second mammalian species (naive PSC2s) until a mosaic colony forms, wherein (a) the PSC1s or the MSC1s comprise a first marker and/or (b) the naive PSC2s comprise a second marker, further wherein, in (a), the mosaic colony is mosaic for the first marker and/or, in (b), the mosaic colony is mosaic for the second marker, and wherein the first mammalian species and the second mammalian species are different species;
  (ii) selecting from the mosaic colony of step (i) a cell group comprising one or more first-marker-positive cells and/or one or more second-marker-negative cells;
  (iii) coculturing the cell group of step (ii) with a host embryo of the second mammalian species (HE2) until the HE2 cocultured with the cell group reaches an early blastocyst stage embryo with an inner cell mass, wherein the host embryo optionally comprises a third marker which is the same or different than the second marker and which third marker is different than the first marker;
  (iv) separating the inner cell mass that comprises cells positive for the first marker and/or cells negative for the second and third markers from the early blastocyst stage embryo of step (iii); and
  (v) cloning from the separated inner cell mass from step (iv), one or more of the cells positive for the first marker and/or one or more of the cells negative for the second and third markers to establish the stem cells capable of forming chimeras between different species;

(B)
  (i) combining PSC1s or MSC1s with naive PSC2s to obtain a cell group, wherein (a) the PSC1s or the MSC1s comprise a first marker and/or (b) the naive PSC2s comprise a second marker, further wherein the first mammalian species and the second mammalian species are different species;
  (ii) coculturing the cell group in step (i) with a HE2 until the HE2 reaches an early blastocyst stage embryo with an inner cell mass, wherein the host embryo optionally comprises a third marker which is the same or different than the second marker and which third marker is different than the first marker;
  (iii) separating the inner cell mass that comprises cells positive for the first marker and/or cells negative for the second and third markers from the early blastocyst stage embryo of step (ii); and
  (iv) cloning from the separated inner cell mass from step (iii), one or more of the cells positive for the first marker and/or one or more of the cells negative for the second and third markers to establish the stem cells capable of forming chimeras between different species;

(C)
  (i) coculturing PSC1s or MSC1s with conspecific mammalian naïve PSCs (naïve cPSCs) until a mosaic colony forms, wherein (a) the PSC1s or the MSC1s comprise a first marker and/or (b) the naive cPSCs comprise a second marker, further wherein, in (a), the mosaic colony is mosaic for the first marker and/or, in (b), the mosaic colony is mosaic for the second marker;
  (ii) selecting from the mosaic colony of step (i) a cell group comprising one or more first-marker-positive cells and/or one or more second-marker-negative cells;
  (iii) coculturing the cell group in step (ii) with a conspecific mammalian host embryo (cHE) until the cHE reaches an early blastocyst stage embryo with an inner cell mass, wherein the embryo optionally comprises a third marker which is same or different as the second marker and which third marker is different than the first marker;
  (iv) separating the inner cell mass that comprises cells positive for the first marker and/or cells negative for the second and third markers from the early blastocyst stage embryo of step (iii); and
  (v) cloning from the separated inner cell mass from step (iv), one or more of the cells positive for the first marker and/or one or more of the cells negative for the second and third markers to establish the stem cells capable of forming chimeras between the same species; or (D)
  (i) combining PSC1s or MSC1s with naïve cPSCs to obtain a cell group, wherein (a) the PSC1s or MSC1s comprise a first marker and/or (b) the naive cPSCs comprise a second marker;
  (ii) coculturing the cell group in step (i) with a cHE until the cHE reaches an early blastocyst stage embryo with an inner cell mass, wherein the cHE optionally comprises a third marker which is the same or different as the second marker and which third marker is different than the first marker;
  (iii) separating the inner cell mass that comprises cells positive for the first marker and/or cells negative for the second and third markers from the early blastocyst stage embryo of step (ii); and (iv) cloning from the separated inner cell mass from step (iii) one or more of the cells positive for the first marker and/or one or more of the cells negative for the second and third markers to establish the stem cells capable of forming chimeras between the same species, wherein, in (A)-(D), the PSC1s or the MSC1s are non-rodent PSCs or MSCs or are rodent induced pluripotent stem cells (iPS cells) or MSCs, further wherein the first and second mammalian species in (A) or (B) are not a human, and wherein the first mammalian species in (C) or (D) is not a human.

2. The method according to claim 1, further comprising combining the stem cells established in step (A)(v) with the naïve PSC2s to obtain a cell group, and repeating steps (A)(iii) to (v).

3. The method according to claim 1, wherein the PSC1s and/or the PSC2s in step (A)(i) are selected from the group consisting of the following: ES cells and iPS cells, and the MSC1s are selected from the group consisting of the following: trophoblast stem cells (TS cells), epiblast stem cells (EpiS cells), embryonic germ cells (EG cells), multipotent germline stem cells (mGS cells), nuclear transfer ES cells (ntES cells), hematopoietic stem cells, neural stem cells, and mesenchymal stem cells.

4. The method according to claim 1, wherein the PSC1s or MSC1s in step (A)(i) are ES cells or iPS cells.

5. The method according to claim 1, wherein the HE2 in step (A)(iii) is selected from the group consisting of an early embryo, a tetraploid embryo, a male embryo, and a parthenogenetic embryo.

6. The method according to claim 1, wherein, in (A), the first mammalian species is selected from the group consisting of a mouse, a rat, a rabbit, a dog, a cat, a horse, cattle, a goat, sheep, a pig, and a monkey, and the second mammalian species is selected from the group consisting of a mouse, a rat, a rabbit, a dog, a cat, a horse, cattle, a goat, sheep, a pig, and a monkey.

7. The method according to claim 1, further comprising repeating steps (B)(i) to (iv), wherein step (B)(i) of one of the repeated steps is performed by combining the stem cells established in step (B) (iv) of the step prior to the repeated step with the naïve PSC2s to obtain a cell group.

8. The method according to claim 1, further comprising combining the stem cells established in step (C)(v) with the naïve cPSCs to obtain a cell group, and repeating steps (C)(iii) to (v).

9. The method according to claim 1, further comprising repeating steps (D)(i) to (v), wherein step (D)(i) of one of the repeated steps is performed by combining the stem cells established in step (D) (iv) of the step prior to the repeated step with the naïve cPSCs to obtain a cell group.

10. The method according to claim 1, wherein the inner cell mass of step (A)(iii), (B)(ii), (C)(iii), or (D)(ii) is a mosaic inner cell mass which comprises:

cells positive for the first marker and cells negative for the first marker; and/or cells negative for the second and third markers and cells positive for the second and/or third marker.

11. The method of claim 1, wherein feeder cells, are added during at least one of the coculturing steps.

12. The method of claim 11, wherein said feeder cells comprise mouse embryonic fibroblasts (MEFs).

13. The method of claim 1, wherein the PSC1s or MSC1s are PSCs.

14. The method according to claim 1, wherein, in (A), the first mammalian species is selected from the group consisting of a cat, cattle, a pig, and a monkey, and the second mammalian species is a mouse.

15. A method for establishing stem cells capable of forming chimeras between different or conspecific species, comprising the following steps:

(A)
(i) coculturing PSC1s or MSC1s with naïve PSC2s until a mosaic colony forms, wherein (a) the PSC1s or the MSC1s comprise a first marker and/or (b) the naive PSC2s comprise a second marker, further wherein, in (a), the mosaic colony is mosaic for the first marker and/or, in (b), the mosaic colony is mosaic for the second marker, and wherein the first mammalian species and the second mammalian species are different species;

(ii) selecting from the mosaic colony of step (i) a cell group comprising one or more first-marker-positive cells and/or one or more second-marker-negative cells;

(iii) coculturing the cell group of step (ii) with a HE2 until the HE2 reaches an early blastocyst stage embryo with an inner cell mass, wherein, the host embryo optionally comprises a third marker which is the same or different than the second marker and which third marker is different than the first marker;

(iv) separating the inner cell mass that comprises cells positive for the first marker and/or cells negative for the second and third markers from the early blastocyst stage embryo of step (iii); and (v) cloning from the separated inner cell mass from step (iv) one or more of the cells positive for the first marker and/or one or more of the cells negative for the second and third markers to establish the stem cells capable of forming chimeras between different species;

(B)
(i) combining PSC1s or MSC1s with naïve PSC2s to obtain a cell group, wherein (a) the PSC1s or the MSC1s comprise a first marker and/or (b) the naive PSC2s comprise a second marker, further wherein the first mammalian species and the second mammalian species are different species;

(ii) coculturing the cell group in step (i) with a HE2 until the HE2 reaches an early blastocyst stage embryo with an inner cell mass, wherein, the host embryo optionally comprises a third marker which is the same or different as the second marker and which third marker is different than the first marker;

(iii) separating the inner cell mass that comprises cells positive for the first marker and/or cells negative for the second and third markers from the early blastocyst stage embryo of step (ii); and (iv) cloning from the separated inner cell mass from step (iii) one or more of the cells positive for the first marker and/or one or more of the cells negative for the second and third markers to establish the stem cells capable of forming chimeras between different species;

(C)
(i) coculturing PSC1s or MSC1s with naïve cPSCs until a mosaic colony forms, wherein (a) the PSC1s or the MSC1s comprise a first marker and/or (b) the naive cPSCs comprise a second marker, further wherein, in (a), the mosaic colony is mosaic for the first marker and/or, in (b), the mosaic colony is mosaic for the second marker;
(ii) selecting from the mosaic colony of step (i) a cell group comprising one or more first-marker-positive cells and/or one or more second-marker-negative cells;
(iii) coculturing the cell group in step (ii) with a cHE until the cHE reaches an early blastocyst stage embryo with an inner cell mass, wherein the cHE optionally comprises a third marker which is the same or different than the second marker and which third marker is different than the first marker;
(iv) separating the inner cell mass that comprises cells positive for the first marker and/or cells negative for the second and third markers from the embryo of step (iii); and
(v) cloning from the separated inner cell mass from step (iv) one or more of the cells positive for the first marker and/or one or more of the cells negative for the second and third markers to establish the stem cells capable of forming chimeras between the same species; or (D)
(i) combining PSC1s or MSC1s with naïve cPSCs to obtain a cell group, wherein (a) the PSC1s or the MSC1s comprise a first marker and/or (b) the naïve cPSCs comprise a second marker;
(ii) coculturing the cell group in step (i) with a cHE until the cHE reaches an early blastocyst stage embryo with an inner cell mass, wherein the cHE optionally comprises a third marker which is the same or different than the second marker and which third marker is different than the first marker;
(iii) separating the inner cell mass that comprises cells positive for the first marker and/or cells negative for the second and third markers from the early blastocyst stage embryo of step (ii); and
(iv) cloning from the separated inner cell mass from step (iii) one or more of the cells positive for the first marker and/or one or more of the cells negative for the second and third markers to establish the stem cells capable of forming chimeras between the same species, wherein, in (A)-(D), the PSC1s or the MSC1s are non-rodent PSCs or MSCs or are rodent iPS cells or MSCs, wherein the first and second mammalian species in (A) or (B) are not a human, and wherein the first mammalian species in (C) or (D) is not a human;

and further wherein: step (A)(iii) is performed by microinjecting or aggregating the cell group of step (A)(ii) into the HE2 followed by the coculture; step (B)(ii) is performed by microinjecting or aggregating the cell group of step (B)(i) into the HE2 followed by the coculture; step (C)(iii) is performed by microinjecting or aggregating the cell group of step (C)(ii) into the cHE followed by the coculture; or step (D)(ii) is performed by microinjecting or aggregating the cell group of step (D)(i) into the HE2 followed by the coculture.

16. The method of claim 15, wherein feeder cells, are added during at least one of the coculturing steps.

17. The method of claim 16, wherein said feeder cells comprise MEFs.

18. The method of claim 15, wherein the PSC1s or MSC1s are PSCs.

19. The method according to claim 15, wherein, in (A), the first mammalian species is selected from the group consisting of a mouse, a rat, a rabbit, a dog, a cat, a horse, cattle, a goat, sheep, a pig, and a monkey, and the second mammalian species is selected from the group consisting of a mouse, a rat, a rabbit, a dog, a cat, a horse, cattle, a goat, sheep, a pig, and a monkey.

20. The method according to claim 15, wherein, in (A), the first mammalian species is selected from the group consisting of a cat, cattle, a pig, and a monkey, and the second mammalian species is a mouse.

* * * * *

SEQUENCE LISTING

```
<160> NUMBER OF SEQ ID NOS: 4

<210> SEQ ID NO 1
<211> LENGTH: 28
<212> TYPE: DNA
<213> ORGANISM: Artificial Sequence
<220> FEATURE:
<223> OTHER INFORMATION: primer

<400> SEQUENCE: 1
cattggagta gtcctactat ttaccgtt                                       28

<210> SEQ ID NO 2
<211> LENGTH: 33
<212> TYPE: DNA
<213> ORGANISM: Artificial Sequence
<220> FEATURE:
<223> OTHER INFORMATION: primer

<400> SEQUENCE: 2
ggattagtag gattagtatt ataaataagg ctc                                 33

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
atcattcata gcctggcaga                                                20
```

```
<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
aaggatgaat atggatttgc                                              20
```